(12) United States Patent
Kennedy et al.

(10) Patent No.: US 11,116,214 B2
(45) Date of Patent: *Sep. 14, 2021

(54) LICE CONTROL COMPOSITION AND METHOD

(71) Applicant: TyraTech, Inc., Morrisville, NC (US)

(72) Inventors: Keith Kennedy, Morrisville, NC (US); Jason Schmidt, Morrisville, NC (US)

(73) Assignee: TYRATECH, INC., Morrisville, NC (US)

( * ) Notice: Subject to any disclaimer, the term of this patent is extended or adjusted under 35 U.S.C. 154(b) by 744 days.

This patent is subject to a terminal disclaimer.

(21) Appl. No.: 15/599,728

(22) Filed: May 19, 2017

(65) Prior Publication Data

US 2017/0318806 A1    Nov. 9, 2017

Related U.S. Application Data

(63) Continuation of application No. 14/776,928, filed as application No. PCT/US2014/000057 on Mar. 17, 2014.

(60) Provisional application No. 61/789,624, filed on Mar. 15, 2013.

(51) Int. Cl.

| A01N 37/36 | (2006.01) |
| A61K 31/045 | (2006.01) |
| A61K 31/11 | (2006.01) |
| A61K 8/34 | (2006.01) |
| A61K 8/37 | (2006.01) |
| A61Q 17/02 | (2006.01) |
| A01N 31/04 | (2006.01) |
| A61K 36/53 | (2006.01) |
| A01N 31/02 | (2006.01) |
| A01N 35/04 | (2006.01) |
| A01N 37/02 | (2006.01) |
| A01N 43/30 | (2006.01) |
| A01N 49/00 | (2006.01) |
| A01N 61/02 | (2006.01) |
| A61K 36/185 | (2006.01) |
| A01N 43/16 | (2006.01) |
| A01N 43/20 | (2006.01) |
| A01N 65/22 | (2009.01) |
| A01N 65/00 | (2009.01) |

(52) U.S. Cl.
CPC ............. *A01N 37/36* (2013.01); *A01N 31/02* (2013.01); *A01N 31/04* (2013.01); *A01N 35/04* (2013.01); *A01N 37/02* (2013.01); *A01N 43/16* (2013.01); *A01N 43/20* (2013.01); *A01N 43/30* (2013.01); *A01N 49/00* (2013.01); *A01N 61/02* (2013.01); *A01N 65/00* (2013.01); *A01N 65/22* (2013.01); *A61K 8/342* (2013.01); *A61K 8/347* (2013.01); *A61K 8/37* (2013.01); *A61K 31/045* (2013.01); *A61K 31/11* (2013.01); *A61K 36/185* (2013.01); *A61K 36/53* (2013.01); *A61Q 17/02* (2013.01); *A01N 2300/00* (2013.01); *A61K 2300/00* (2013.01)

(58) Field of Classification Search
CPC ..................................................... A01N 37/36
See application file for complete search history.

(56) References Cited

U.S. PATENT DOCUMENTS

| 7,541,155 | B2 | 6/2009 | Enan |
| 7,622,269 | B2 | 11/2009 | Enan |
| 8,231,887 | B2 | 7/2012 | Sims |
| 8,501,247 | B2 | 8/2013 | Enan et al. |
| 8,507,013 | B2 | 8/2013 | Enan |
| 8,685,471 | B2 | 4/2014 | Enan |
| 8,691,256 | B2 | 4/2014 | Enan |
| 8,734,869 | B2 | 5/2014 | Enan |
| 8,834,908 | B2 | 9/2014 | Jones |
| 8,865,230 | B2 | 10/2014 | Enan |
| 9,492,490 | B1 | 11/2016 | Enan |
| 2004/0028714 | A1* | 2/2004 | Blondeau ............... A01N 37/18 424/405 |
| 2006/0263403 | A1 | 11/2006 | Enan |
| 2008/0047312 | A1 | 2/2008 | Hill et al. |
| 2008/0075796 | A1 | 3/2008 | Enan |
| 2008/0145462 | A1 | 6/2008 | Enan |
| 2008/0187607 | A1 | 8/2008 | Bessette |
| 2009/0099135 | A1 | 4/2009 | Enan |
| 2009/0232918 | A1 | 9/2009 | Enan |
| 2009/0263515 | A1* | 10/2009 | Bessette ................. A01N 65/00 424/739 |
| 2011/0003317 | A1 | 1/2011 | Enan |

(Continued)

FOREIGN PATENT DOCUMENTS

| WO | WO 2008/101131 A1 | 8/2008 |
| WO | WO 2010/117740 A2 | 10/2010 |

(Continued)

OTHER PUBLICATIONS

U.S. Appl. No. 16/049,033, filed Jul. 30, 2018.
U.S. Appl. No. 16/051,875, filed Aug. 1, 2018.
Soap Queen by Bramble Berry, "When Mold Strikes", Sep. 12, 2008, retrieved from https://www.soapqueen.com/bath-and-body-tutorials/lotion/when-mold-stikes-2/.
Flick, E.W., Industrial Surfactants: 2nd Edition, Stepan Co. WAC, 1993, p. 467.
U.S. Appl. No. 16/171,807, filed Oct. 26, 2018.
U.S. Appl. No. 16/266,451, filed Feb. 4, 2019.

(Continued)

*Primary Examiner* — Amy L Clark
(74) *Attorney, Agent, or Firm* — K&L Gates LLP

(57) ABSTRACT

The present invention generally relates to compositions and methods related to controlling arthropods. Embodiments of the invention include compositions for controlling an arthropod, which can include one or more plant essential oils and methods for using these compositions. The plant essential oils, when combined, can have a synergistic effect. Embodiments of the invention relate to compositions and methods related to controlling lice.

5 Claims, 8 Drawing Sheets

(56) References Cited

U.S. PATENT DOCUMENTS

| | | | |
|---|---|---|---|
| 2011/0008471 | A1 | 1/2011 | Enan |
| 2011/0171135 | A1* | 7/2011 | Enan .................. A01N 31/08 |
| | | | 424/9.2 |
| 2012/0087871 | A1 | 4/2012 | Schneidmiller et al. |
| 2013/0034619 | A1 | 2/2013 | Nys |
| 2014/0377385 | A1 | 12/2014 | Enan |
| 2015/0087516 | A1 | 3/2015 | Enan |
| 2015/0150838 | A1 | 6/2015 | Enan et al. |
| 2015/0201615 | A1 | 7/2015 | Schmidt et al. |
| 2016/0029625 | A1 | 2/2016 | Kennedy et al. |
| 2016/0165899 | A1 | 6/2016 | Bissinger et al. |
| 2018/0035674 | A1 | 2/2018 | Schmidt et al. |

FOREIGN PATENT DOCUMENTS

| | | |
|---|---|---|
| WO | WO 2013/050967 A1 | 4/2013 |
| WO | WO 2014/063109 A1 | 4/2014 |

OTHER PUBLICATIONS

U.S. Appl. No. 16/457,297, filed Jun. 28, 2019.

Salafsky et al., "Short Report: Study on the Efficacy of a New Long-Acting Formulation of N, N-Diethyl-m-Toluamide (Deet) for the Prevention of Tick Attachment", Am. J. Trop. Med. Hyg.,2000, vol. 62, No. 2, pp. 169-172.

Carroll et al., "Twelve-hour duration testing of cream formulations of three repellents against Amblyomma americanum", Medical and Veterinary Entomology, 2008, vol. 22, pp. 144-151.

Kimps et al., "First report of the repellency of 2-tridecanone against ticks", Medical and Veterinary Entomology, 2011, vol. 25, pp. 202-208.

Bissinger et al., "Efficacy of the new repellent BioUD against three species of ixodid ticks", Exp Appl Acarol, 2009, vol. 48, pp. 239-250.

Bissinger et al., "Novel field assays and the comparative repellency of BioUDO, Deet and permethrin against Amblyomma americanum", Medical and Veterinary Entomology, 2011, vol. 25, pp. 217-226.

Barnard, D., "Repellency of Essential Oils to Mosquitoes (Diptera: Culicidae)", J. Med. Entomol., Sep. 1999, vol. 36, No. 5, pp. 625-629.

Shulaev et al., "Airborne signalling by methyl salicylate in plant pathogen resistance", Nature, vol. 382, Feb. 1997, pp. 718-721.

James et al., "Field-Testing of Methyl Salicylate for Recruitment and Retention of Beneficial Insects in Grapes and Hops", Journal of Chemical Ecology, Aug. 2004, vol. 30, No. 8, pp. 1613-1628.

Downs et al., "Evidence for double resistance to permethrin and malathion in head lice", British Journal of Dermatology, 1999, vol. 141, pp. 508-511.

Lei et al., "Nematicidal activity of two monoterpenoids and SER-2 tyramine receptor of Caenorhabditis elegans", Biochemical Pharmacology, 2010, vol. 79, pp. 1062-1071.

Johnson et al., Chapter 12, Synthetic Fatty Acids, "Fatty Acids in Industry, Processes, Properties, Derivatives, Applications", Marcel Dekker, Inc., 1989, pp. 277-326.

U.S. Appl. No. 15/286,110, filed Oct. 5, 2016.
U.S. Appl. No. 15/878,940, filed Jan. 24, 2018.

* cited by examiner

LICE CONTROL COMPOSITION AND METHOD

RELATED APPLICATIONS

This application claims priority under 35 U.S.C. § 120 from co-pending U.S. patent application Ser. No. 14/776,928, filed Sep. 15, 2015, which in turn claims the benefit of U.S. Provisional Patent Application No. 61/789,624, filed Mar. 15, 2013, the entire text whereof is incorporated by reference into the present application.

FIELD OF THE INVENTION

The invention disclosed herein generally relates to compositions and methods related to controlling arthropods, namely order Phthiraptera.

BACKGROUND

Arthropods are invertebrate animals with jointed limbs, a segmented body, and an exoskeleton. They belong to the phylum Arthropoda and include, but are not limited to arachnids, crustaceans, and insects.

Louse (plural: lice) is the common name for members of over 3,000 species of wingless insects of the order Phthiraptera; three of which are classified as human disease agents. Phthiraptera belong to the phylum Arthropoda. They are obligate ectoparasites of every avian and mammalian order except for monotremes (the platypus and echidnas), bats, whales, dolphins, porpoises and pangolins.

One of the most commonly transmitted conditions in pre-school and elementary school-age children is head lice (*Pediculus humanus capitis*). It is estimated about 6 to 12 million infestations occur yearly in the United States in children age 3 to 12 years. Head lice are usually spread by direct contact with the hair of an infected person. This can occur while children play on the playground at school or at home or during team sporting activities. Also, lice can spread through the use of combs, brushes, hats, and/or bedding of someone with an infestation.

The main symptoms of an infestation of head lice are intense scalp itching, perhaps even a tickling or crawling sensation on the scalp. There may be small red bumps on the scalp, neck or shoulders and the presence of nits (eggs). Lice are most active at night so they can disturb the sleep. Diagnosis is made by observing a louse crawling on the scalp or more frequently, observation of the nits on the hairs at the base of the neck or behind the ears. Commonly, it is the teachers or school personnel who find the infestation causing all families at the school to be notified and/or treated.

Treatment involves topical medication on the scalp as well as steps to kill the lice and nits in the home and on personal belongings of those with infestations (washing and/or replacement of combs, hair brushes, and bedding). The hair of those with the infestation are treated with topical medications contain a pediculicide, namely, pyrethrins plus piperonyl butoxide (e.g., RID®), permethrin (e.g., NIX®), lindane (e.g., KWELL®), or malathion (e.g., OVIDE®). Additional homeopathic treatments are also available. Ovicidal activity is an essential part of an effective head lice treatment program.

Currently, the American Academy of Pediatrics recommends the use of NIX® with retreatment within 7 to 10 days if live lice are still present. However, no treatment is considered 100% effective often requiring repeat treatment.

The incidence of head lice is increasing and the success of current treatments is declining. Over the counter products are becoming less effective because lice are becoming resistant to the active ingredients in such products. Recent clinical tests of head lice treatments have found that the most used, the pyrethroids and organophosphates, have success rates of only 13% and 36%, respectively (Downs, A. M., et al. (1999). Evidence for double resistance to permethrin and malathion in head lice. British Journal of Dermatology 141(3), 508-511). In addition, a recent study of 2800 children carried out by the Liverpool School of Hygiene and Tropical Medicine and the National Public Health Service for Wales found that two thirds of head lice were resistant to pyrethroid-based head lice products. Pyrethroids are the active ingredient in many popular mousse and lotion products. Further, prescription treatments designed to overcome some of these resistance issues are equally problematic in that they contain strong synthetic chemicals (some of which have even been banned for use as contact insecticides) that may cause other health problems.

The increase in resistance is partly as a result of misuse of head lice treatments. If a product is not used according to the directions on the packaging, head lice are exposed to lower levels of insecticide. These "sub-lethal" levels are not enough to kill all the lice on the scalp and thus allow the "fittest" lice to survive and breed. Resistance has also arisen because the most popular products have a single mechanism of action, targeting a single part of the nervous system of the louse. This makes it much easier for head lice to overcome these products and to become resistant. Naturally derived insecticides may provide benefits in managing head lice resistance. Naturally derived insecticides have multiple, or alternative, modes of action against insects, interfering with their feeding, growth and reproduction. Accordingly, lice cannot overcome these products with only a single genetic change as they can with synthetic products.

Formulation can play a critical role in extending efficacy. For example, a liposomal formulation of DEET provided complete protection on treated rabbits against attachment of adult *D. variabilis* and *A. americanum* ticks for 72 h compared to no protection by a standard formulation of DEET (Salafsky, B., et al. (2000). Study on the efficacy of a new long-acting formulation of N, N-diethyl-m-toluamide (DEET) for the prevention of tick attachment. *American Journal of Tropical Medical and Hygiene*, 62(2), 169-172). In another study, a polymer formulation of DEET and cream formulations of Picaridin and SS220 provided almost complete repellency to nymphal *A. americanum* for 12 h (Carroll, J. F., et al. (2008). Twelve-hour duration testing of cream formulations of three repellents against *Amblyomma americanum*. *Medical and Veterinary Entomology*, 22(2), 144-151). The plant-derived repellent, unformulated 2-undecanone provided 74% repellency against *D. variabilis* 2 h after application (Kimps, N. W., et al. (2011). First report of the repellency of 2-tridecanone against ticks. *Medical and Veterinary Entomology*, 25(2), 202-208) compared to 98% repellency from 3-3.5 h after application when formulated in the product BIOUD® (Bissinger, B. W., et al. (2009). Efficacy of the new repellent BIOUD® against three species of ixodid ticks. *Experimental and Applied Acarology*, 48(3), 239-250). Most published research has focused on repellent active ingredient identification rather than formulation and formulation chemistry is often a guarded secret of private industries (Bissinger, B. W., et al. (2011). Novel field assays and the comparative repellency of BIOUD$^e$, DEET, and permethrin against *Amblyomma americanum*. *Medical and Veterinary Entomology*. 25: 217-226).

A number of plant-based, natural, or non-toxic arthropod control products are available commercially; in many cases because of their rapid registration process under the US EPA's FIFRA section 25(b), which provides exemption from federal registration for specific ingredients that are deemed demonstrably safe for their intended use. Many of the ingredients on the 25(b) list are highly volatile compounds, causing them to provide only short-term control duration. Increasing the concentration of active ingredient can lengthen the duration of repellency; however, many essential oils are irritating to the skin above a certain concentration (Barnard, D. R. (1999). Repellency of essential oils to mosquitoes (Diptera: Culicidae). *Journal of Medical. Entomology,* 36(5), 625-629). Additionally, the aesthetics (e.g., odor, appearance, tactile, residual odor, discoloration, etc.) of many plant-based repellents are poor. Therefore, there is a need for an arthropod control composition that provides a high level of efficacy for an extended amount of time while simultaneously exhibiting desirable aesthetics, such as pleasant odor and skin feel.

One advantage of the present compositions used in the methods of the present invention is that compositions can be produced containing only ingredients exempt from EPA registration by virtue of their appearance on the FIFRA 25(b) list or Class 4(a) inert ingredient list making the composition completely safe for use, and potentially eligible for classification as an organic pest control agent.

SUMMARY OF THE INVENTION

Embodiments of the invention include compositions for control of arthropods. Some of such compositions can contain geraniol, vanillin, isopropyl myristate, and triethyl citrate, as well as, in some cases, other ingredients. For example, in some embodiments, the compositions can include isopropyl alcohol and butyl lactate. Likewise, they can further include benzyl alcohol. The composition can also include thyme oil white, linalool, THL and/or heliotropine. In some embodiments, the compositions can include lauric acid, white mineral oil and vitamin e in combination with any or all of the forgoing ingredients.

The compositions can be used in various formulations which can optionally include a carrier, a surface active agent, and/or a surfactant. The can be formulated, for example, as: a water-based formulation, a dust formulation, a spray formulation, a burning formulation, and the like.

Embodiments of the invention also include methods for controlling arthropods using the formulations as described herein, and including steps such as, for example, applying the formulation to a desired host, area, or object; and controlling arthropods wherein at least 1% of the arthropods exposed to the formulation die. In some embodiments, at least 50% of arthropods exposed to the formulation are repelled from the host, area or object. In some embodiments, at least 50% of arthropods exposed to the formulation display reduced motility.

DETAILED DESCRIPTION OF THE INVENTION

Figure 1:
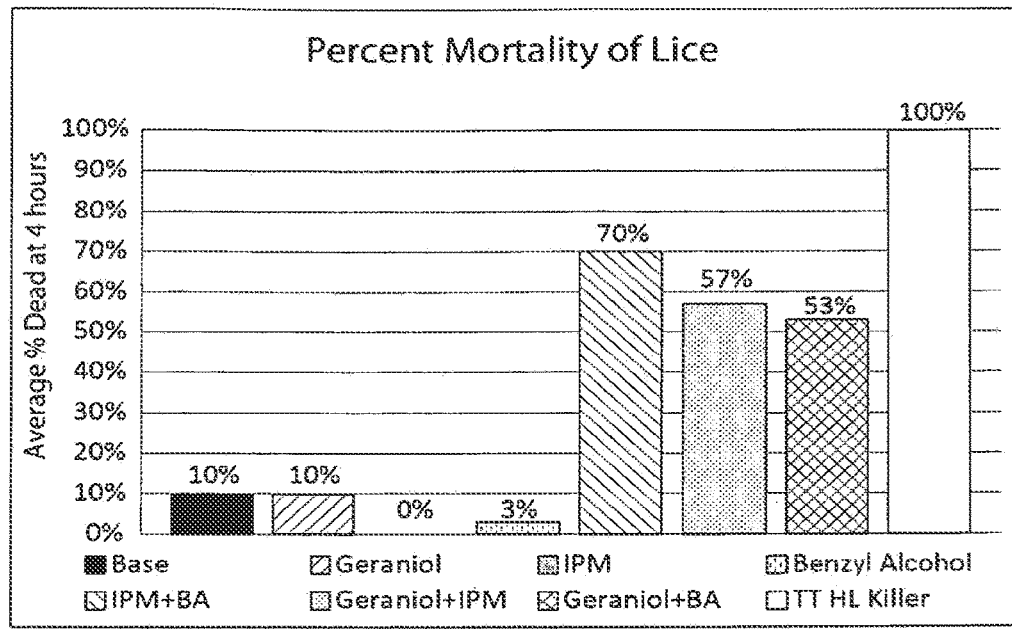
FIG. 1 shows the percentage mortality of lice 4 hours after treatment with various compositions.

Unless otherwise noted, terms are to be understood according to conventional usage by those of ordinary skill in the relevant art.

The present invention generally relates to compositions and methods related to controlling arthropods. More specifically, the present invention relates to compositions and methods related to controlling lice.

The compositions and methods of the invention can used to control any type of arthropod, such as an insect. Exemplary arthropods that can be controlled include but are not limited to beetles, cockroaches, flies, ants, larvae, bees, lice, fleas, mosquitoes, moths, and the like. Exemplary arthropod orders can include but are not limited to orders Acari, Anoplura, Araneae, Blattodea, Coleoptera, Collembola, Diptera, Grylloptera, Hemiptera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, and Thysanoptera and the like.

The compositions and methods of the invention can used to control any type of lice (order Phthiraptera) including Anoplura (sucking lice) and Mallophaga (chewing lice). Exemplary suborders of lice that can be controlled include but are not limited to, Anoplura (occurring on mammals); Rhyncophthirina (parasites of elephants and warthogs); Ischnocera (mostly avian chewing lice); and Amblycera (a primitive suborder of chewing lice, widespread on birds, however, also live on South-American and Australian mammals) and the like. Exemplary arthropod orders can include but are not limited to orders Acari, Anoplura, Araneae, Blattodea, Coleoptera, Collembola, Diptera, Grylloptera, Hemiptera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, and Thysanoptera and the like.

Embodiments of the invention include compositions for controlling an arthropod, which can include one or more plant essential oils and methods for using these compositions. The plant essential oils, when combined, can have a synergistic effect. The compositions also can include a fixed oil, which is typically a non-volatile non-scented plant oil. Additionally, in some embodiments, these compositions can be made up of generally regarded as safe (GRAS) compounds.

For purposes of simplicity, the term "arthropod" shall be used in this application; however, it should be understood that the term "arthropod" refers, not only to insects, but also to lice, mites, spiders, ticks, arachnoids, arachnids, larvae, parasites, and like invertebrates. Also for purposes of this application, the term "arthropod control" shall refer to having a repellent effect, a pesticidal effect, or both.

"Repellent effect" is an effect wherein more arthropods are repelled away from a host or area that has been treated with the composition than a control host or area that has not been treated with the composition. In some embodiments, repellent effect is an effect wherein at least about 50% of arthropods are repelled away from a host or area that has been treated with the composition. In some embodiments, repellent effect is an effect wherein at least about 75% of arthropods are repelled away from a host or area that has been treated with the composition. In some embodiments, repellent effect is an effect wherein at least about 90% of arthropods are repelled away from a host or area that has been treated with the composition. In some embodiments, repellent effect is an effect wherein at least about 95% of arthropods are repelled away from a host or area that has been treated with the composition.

"Pesticidal effect" is an effect wherein treatment with a composition causes at least about 1% of the arthropods to die. In this regard, an LC1 to LC100 (lethal concentration) or an LD1 to LD100 (lethal dose) of a composition will cause a pesticidal effect. In some embodiments, the pesticidal effect is an effect wherein treatment with a composition causes at least about 5% of the exposed arthropods to die.

In some embodiments, the pesticidal effect is an effect wherein treatment with a composition causes at least about 10% of the exposed arthropods to die. In some embodiments, the pesticidal effect is an effect wherein treatment with a composition causes at least about 25% of the arthropods to die. In some embodiments the pesticidal effect is an effect wherein treatment with a composition causes at least about 50% of the exposed arthropods to die. In some embodiments the pesticidal effect is an effect wherein treatment with a composition causes at least about 75% of the exposed arthropods to die. In some embodiments the pesticidal effect is an effect wherein treatment with a composition causes at least about 90% of the exposed arthropods to die.

In some embodiments of the invention, treatment with compositions of the invention will result in a knockdown of the arthropod occurring within a few seconds to a few minutes. "Knockdown" is an effect wherein treatment with a composition causes at least about 1% of the exposed arthropods to display reduced mobility. In some embodiments, the knockdown is an effect wherein treatment with a composition causes at least about 50% of the exposed arthropods to display reduced mobility.

The compositions of the present invention can be used to control arthropods by either treating a host directly, or treating an area in which the host will be located, for example, an indoor living space, outdoor patio or garden. For purposes of this application, host is defined as a plant, human, mammal, or other animal.

Treatment can include use of an oil-based formulation, a water-based formulation, an alcohol-based formulation, a residual formulation, and the like. In some embodiments, combinations of formulations can be employed to achieve the benefits of different formulation types.

Embodiments of the invention are directed to compositions for controlling arthropods and methods for using these compositions. In some embodiments, the compositions can include compounds that are generally regarded as safe (GRAS compounds). In some embodiments, the compositions can include compounds of a plant origin, such as plant essential oils or monoterpenoids of plant essential oils. In some embodiments, the compositions include two or more compounds. In some embodiments, the compositions can include any of the following oils, or mixtures thereof:

Methyl salicylate, also known as *betula* oil. Methyl salicylate is a major component of oil of wintergreen and is sometimes referred to interchangeably with oil of wintergreen. It is a natural product of many species of plants, is the methyl ester of salicylic acid, and can be produced chemically from the condensation reaction of salicylic acid and methanol. Some of the plants producing it are called wintergreens, hence the common name. Methyl salicylate can be used by plants as a pheromone to warn other plants of pathogens (Shulaev, et al. Airborne signalling by methyl salicylate in plant pathogen resistance (1997) Nature, 385, 718-721). The release of methyl salicylate can also function as an exopheromone aid in the recruitment of beneficial insects to kill the herbivorous insects (James and Price (2004) Field-Testing of Methyl Salicylate for Recruitment and Retention of Beneficial Insect in Grapes and Hops. *Journal of Chemical Ecology*, 30(8), 1613-1628). Numerous plants produce methyl salicylate including species of the family Pyrolaceae and of the genera *Gaultheria* and *Betula*. It is noted that, where a given blend or formulation or other composition is disclosed herein as containing wintergreen oil, an alternative embodiment, containing methyl salicylate in place of wintergreen oil, is also contemplated. Likewise, where a blend or formulation of other composition includes methyl salicylate, an alternative embodiment, containing wintergreen oil, is also contemplated.

Thyme Oil is a natural product that can be extracted from certain plants, including species from the Labiatae family; for example, thyme oil can be obtained from *Thymus vulgaris* (also known as, *T. ilerdensis, T aestivus*, and *T. velantianus*), generally by distillation from the leafy tops and tender stems of the plant. Two commercial varieties of thyme oil are recognized, the 'red,' the crude distillate, which is deep orange in color, and the 'white,' which is colourless or pale yellow, which is the 'red' rectified by re-distilling. Thyme oil principally contains the phenols thymol and carvacrol, along with borneol, linalool, and cymene, and rosmarinic and ursolic acids. Where an embodiment describes the use of thyme oil white, other embodiments are specifically contemplated in which the thyme oil white is replaced by thyme oil red, thymol, carvacrol, borneol, linalool, cymene, rosmarinic acid, ursolic acid, or a mixture of any of these with each other or with thyme oil white. Particularly preferable are mixtures of thyme oil white and thyme oil red that contain 10% or less thyme oil red, more preferably 5% or less, and most preferably 1%.

Thymol is a monoterpene phenol derivative of cymene, $C_{10}H_{13}OH$, isomeric with carvacrol, found in thyme oil, and extracted as a white crystalline substance. It is also known as hydroxycymene and 5-methyl-2-(1-methylethyl) phenol. Where an embodiment describes the use of thymol, other embodiments are specifically contemplated in which the thymol is replaced by carvacrol, thyme oil white, thyme oil red, or a mixture of any of these with each other or with thyme oil white.

Geraniol, also called rhodinol and 3,7-dimethyl-2,6-octadien-1-ol, is a monoterpenoid and an alcohol. It is the primary part of oil-of-rose and palmarosa oil. It is used in perfumes and as a flavoring. It is also produced by the scent glands of honey bees to help them mark nectar-bearing flowers and locate the entrances to their hives. Geraniol can be obtained in a highly pure form as Geraniol Fine, FCC (Food Chemicals Codex grade), which is 98% minimum pure geraniol and 99% minimum nerol and geraniol. Geraniol can also be obtained, for example, as Geraniol 60, Geraniol 85, and Geraniol 95. When Geraniol is obtained as Geraniol 60, Geraniol 85, or Geraniol 95, then about forty percent, fifteen percent, or five percent of the oil can be nerol. Nerol is a monoterpene ($C_{10}H_{18}O$), the cis-isomer of geraniol, which can be extracted from attar of roses, oil of orange blossoms and oil of lavender. Citral (3,7-dimethyl-2,6-octadienal or lemonal) is the generic name for the aldehyde form of nerol and geraniol, and can be obtained from lemon myrtly, *Litsea cubeba*, lemongrass, Lemon verbena, lemon balm, lemon, and orange. The E-isomer of citral is known as geranial or citral A. The Z-isomer is known as neral or citral B. Where an embodiment describes the use of any form of geraniol, other embodiments are specifically contemplated in which the geraniol is replaced by another form of geraniol (such as Geraniol Fine FCC or any geraniol/nerol mixture), nerol, geranial, neral, citral, or a mixture of any of these with each other or with any form of geraniol. Similarly, where an embodiment describes the use of any form of citral, other embodiments are specifically contemplated in which the citral is replaced by a form of geraniol (such as Geraniol Fine FCC or any geraniol/nerol mixture), nerol, geranial, neral, or a mixture of any of these with each other or with citral.

Vanillin (also known as methyl vanillin, vanillic aldehyde, vanilin, and 4-hydroxy-3-methoxybenzaldehyde) is the primary component of the extract of the vanilla bean. In addition to vanillin, natural vanilla extract also contains p-hydroxybenzaldehyde, vanillic acid, piperonal, and p-hydroxybenzoic acid. Synthetic vanillin is used as a flavoring agent in foods, beverages, and pharmaceuticals. Where an embodiment describes the use of vanillin, other embodiments are specifically contemplated in which the vanillin is replaced by natural vanilla extract, p-hydroxybenzaldehyde, vanillic acid, piperonal, ethyl vanillin, or p-hydroxybenzoic acid, or a mixture of any of these with each other or with vanillin.

Lime oil is derived from *Citrus aurantifolia* (also known as *Citrus medica* var. acids and *C. latifolia*) of the Rutaceae family and is also known as Mexican and West Indian lime, as well as sour lime. Its chief constituents are α-pinene, β-pinene, camphene, myrcene, p-cymene, d-limonene, γ-terpinene, terpinolene, 1,8-ceneole, linalool, terpinene-4-ol, α-terpineol, neral, geraniol, neral acetate, geranyl acetate, caryophyllene, trans-α-bergamotene, β-Bisabolen, borneol, and citral. It can be obtained in several forms, including Lime Oil 410 (an artificial Mexican-exressed lime oil available from Millennium Specialty Chemicals). Where an embodiment describes the use of any form of lime oil, other embodiments are specifically contemplated in which the lime oil is replaced by α-pinene, β-pinene, camphene, myrcene, p-cymene, d-limonene, γ-terpinene, terpinolene, 1,8-ceneole, linalool, terpinene-4-ol, α-terpineol, neral, geraniol, neral acetate, geranyl acetate, caryophyllene, trans-α-bergamotene, β-Bisabolen, borneol, or citral, or a mixture of any of these with each other or with any form of lime oil.

Black seed oil is obtained from the seeds of *Nigella sativa*. Its chief constituents are carvone, α-pinene, sabinene, β-pinene, and p-cymene, as well as the fatty acids myristic acid, palmitic acid, palmitoleic acid, stearic acid, oleic acid, linoleic acid, linolenic acid, and arachidic acid. Where an embodiment describes the use of any form of black seed oil, other embodiments are specifically contemplated in which the black seed oil is replaced by d-carvone, l-carvone, a racemic mixture of d-carvone and l-carvone, α-pinene, sabinene, β-pinene, or p-cymene, or a mixture of any of these with each other, with any of myristic acid, palmitic acid, palmitoleic acid, stearic acid, oleic acid, linoleic acid, linolenic acid, or arachidic acid or with any form of black seed oil.

Linalool is a naturally-occurring terpene alcohol chemical found in many flowers and spice plants. It is also known as 3,7-dimethylocta-1,6-dien-3-ol. It has two stereoisomeric forms: (S)-(+)-linalool (known as licareol) and (R)-(−)-linalool (known as coriandrol). Linalool can be obtained as linalool coeur (a racemic mixture, CAS number 78-70-6), or in preferred derivative forms such as tetrahydrolinalool (the saturated form), ethyl linalool, linalyl acetate, and pseudo linalyl acetate (7-octen-2-ol, 2-methyl-6-methylene:acetate). Where an embodiment describes the use of any form of linalool, other embodiments are specifically contemplated in which the linalool is replaced by licareol, coriandrol, tetrahydrolinalool, ethyl linalool, linalyl acetate, pseudo linalyl acetate, or a mixture of any of these with each other or with any form of linalool. Similarly, where an embodiment describes the use of tetrahydrolinalool, other embodiments are specifically contemplated in which the tetrahydrolinalool is replaced by licareol, coriandrol, racemic linalool, ethyl linalool, linalyl acetate, pseudo linalyl acetate, or a mixture of any of these with each other or with tetrahydrolinalool. Additionally, where an embodiment describes the use of ethyl linalool, other embodiments are specifically contemplated in which the ethyl linalool is replaced by licareol, coriandrol, tetrahydrolinalool, racemic linalool, linalyl acetate, pseudo linalyl acetate, or a mixture of any of these with each other or with ethyl linalool. Finally, where an embodiment describes the use of linalyl acetate, other embodiments are specifically contemplated in which the linalyl acetate is replaced by licareol, coriandrol, tetrahydrolinalool, racemic linalool, ethyl linalool, pseudo linalyl acetate, or a mixture of any of these with each other or with linalyl acetate.

Isopropyl myristate is the ester of isopropanol and myristic acid; it is also known as 1-tetradecanoic acid, methylethyl ester, myristic acid isopropyl ester, and propan-2-yl tetradecanoate. Where an embodiment describes the use of isopropyl myristate, other embodiments are specifically contemplated in which isopropyl myristate may be replaced by similar chemicals such as isopropyl palmitate, isopropyl isothermal, putty stearate, isostearyl neopentonate, myristyl myristate, decyl oleate, octyl sterate, octyl palmitate, isocetyl stearate, or PPG myristyl propionate, or a mixture of any of these with each other or with isopropyl myristate. Isopropyl myristate may also be used as a thickening agent and emollient.

Piperonal (heliotropine, protocatechuic aldehyde methylene ether) is an aromatic aldehyde that comes as transparent crystals, $C_8H_6O_3$, and has a floral odor. It is used as flavoring and in perfume. It can be obtained by oxidation of piperonyl alcohol. Where an embodiment describes the use of piperonal, other embodiments are specifically contemplated in which piperonal may be replaced by piperonyl alcohol, 3,4-methylenedioxybenzylamine, 3,4-methylenedioxymandelonitrile, piperonylic acid, piperonyl acetate, piperonylacetone, piperonylideneacetone, piperonyl isobutyrate, piperonyl butoxide, piperonylglycine, or protocatecheuic acid or a mixture of any of these with each other or with piperonal. Similarly, where an embodiment describes the use of piperonyl alcohol, other embodiments are specifically contemplated in which piperonyl alcohol may be replaced by piperonal, 3,4-methylenedioxybenzylamine, 3,4-methylenedioxymandelonitrile, piperonylic acid, piperonyl acetate, piperonylacetone, piperonylideneacetone, piperonyl isobutyrate, piperonyl butoxide, piperonylglycine, or protocatecheuic acid, or a mixture of any of these with each other or with piperonyl alcohol.

Triethyl citrate (also known as citric acid, triethyl ester; TEC; ethyl citrate; 2-hydroxy-1,2,3-propanetricarboxylic acid, triethyl ester; and Citroflex 2) is used as a high boiling solvent and plasticizer for vinyl resins and cellulose acetates. It is a plasticizer permitted in the field of food additives, food contact materials, medicines, and pharmaceuticals. Where an embodiment describes the use of triethyl citrate, other embodiments are specifically contemplated in which triethyl citrate may be replaced by other citrate plasticiser esters such as tributyl citrate, acetyl tributyl citrate and tri-(2-ethylhexyl)-citrate, or a mixture of any of these with each other or with triethyl citrate.

Terpines are a class of organic compounds derived from hydrocarbon isoprene ($C_5H_8$) units. Terpines are constituents of essential oils of many plants and flowers. There are many types of terpenes, which are classified by the number of isoprene units in the molecule; examples include monoterpenes and sesquiterpenes. The terpinenes are isomeric hydrocarbons classified as terpenes. Some members of this group are used in a wide variety of flavor and fragrance compositions, as well as in extensions of citrus oils. Gamma-terpinene is also known as 1-isopropyl-4-methyl-1,4-cyclohexadiene, 4-methyl-1-(1-methylethyl)-1,4-cyclohexadiene, and p-mentha-1,4-diene. Alpha-terpinene is also known as 4-methyl-1-(1-methylethyl)-1,3-cyclohexadiene. Both alpha- and gamma-terpinene have a lemony fragrance. Beta-terpinene, also known as 4-methylene-1-(1-methylethyl)cyclohexene, has been prepared from sabinene. A derivative, terpinene-4-ol, is the primary active ingredient of tea tree oil and the compound of highest concentration in essential oil of nutmeg. Other monoterpene alcohol derivatives of the erpinenes include the α-, β-, and γ-terpineol isomers; the α-terpineol isomer is the major component of the naturally isolated terpineol. Other related compounds are terpinolene (4-isopropylidene-1-methylcyclohexene; p-menth-1,4(8)-diene; 1-methyl-4-(1-methylethylidene)cyclohexene; 1-methyl-4-propan-2-ylidene-cyclohexene), and the isomers α-phellandrene and β-phellandrene. Where an embodiment describes the use of gamma-terpinene, other embodiments are specifically contemplated in which gamma-terpinene may be replaced by other terpinenes or derivatives thereof such as terpinolene, α-phellandrene, β-phellandrene, alpha-terpinene, beta-terpinene, α-terpineol, β-terpineol, γ-terpineol, or terpinene-4-ol, or a mixture of any of these with each other or with gamma-terpinene. Where an embodiment describes the use of alpha-terpinene, other embodiments are specifically contemplated in which alpha-terpinene may be replaced by other terpinenes or derivatives thereof such as terpinolene, α-phellandrene, β-phellandrene, gamma-terpinene, beta-terpinene, α-terpineol, β-terpineol, γ-terpineol, or terpinene-4-ol, or a mixture of any of these with each other or with alpha-terpinene. Where an embodiment describes the use of terpinene-4-ol, other embodiments are specifically contemplated in which terpinene-4-ol may be replaced by other terpinenes or derivatives thereof such as terpinolene, α-phellandrene, β-phellandrene, alpha-terpinene, beta-terpinene, α-terpineol, β-terpineol, γ-terpineol, or gamma-terpinene, or a mixture of any of these with each other or with terpinene-4-ol. Where an embodiment describes the use of α-terpineol, other embodiments are specifically contemplated in which α-terpineol may be replaced by other terpinenes or derivatives thereof such as terpinolene, α-phellandrene, β-phellandrene, alpha-terpinene, beta-terpinene, terpinene-4-ol, β-terpineol, γ-terpineol, or gamma-terpinene, or a mixture of any of these with each other or with α-terpineol. Where an embodiment describes the use of terpinolene, other embodiments are specifically contemplated in which terpinolene may be replaced by other terpinenes or derivatives thereof such as α-terpineol, α-phellandrene, β-phellandrene, alpha-terpinene, beta-terpinene, terpinene-4-ol, β-terpineol, γ-terpineol, or gamma-terpinene, or a mixture of any of these with each other or with terpinolene.

In addition, the use of several long-chain aldehydes, such as octanal, nonanal, decanal, and dodecanal. Where an embodiment describes the use of one such aldehyde, other embodiments are specifically contemplated in which the designated aldehyde is replaced with any of the other aldehydes, or a mixture of any of these aldehydes with each other or with the designated aldehyde.

Tocopherols are a class of chemicals consisting of various methylated phenols, some of which have vitamin E activity. These include α-tocopherol, β-tocopherol, γ-tocopherol, and δ-tocopherol. Also belonging to this family are the tocotrienols, including α-tocotrienol, β-tocotrienol, γ-tocotrienol, and δ-tocotrienol. In preferred embodiments, mixtures of these compositions, such as tocopherol gamma tenox or Tenox GT, are employed. Where an embodiment describes the use of one tocopherol, other embodiments are specifically contemplated in which the designated tocopherol is replaced with any of the other tocopherols, or a mixture of any of these tocopherols with each other or with the designated tocopherol.

Fatty acids, suitable for use herein, can be obtained from natural sources such as, for instance, plant or animal esters (e.g., palm oil, rape seed oil, palm kernel oil, coconut oil, babassu oil, soybean oil, castor oil, tallow, whale or fish oils, grease, lard, and mixtures thereof). Fatty acids derived from plant sources are preferred. Normally purified or distilled unsaturated and/or saturated fatty acids will be employed, but naturally occurring mixtures may also be used where appropriate, e.g. when high in unsaturated fatty acids such as soybean, linseed, sunflower, corn, onagra, and/or borage, oil fatty acids. The fatty acids may also be synthetically prepared, for example as described in Johnson, R. W and Fritz, E. (1989) *Fatty Acids in Industry: Processes, Properties, Derivatives, Applications*. New York, N.Y.: Marcel Dekker Inc.

The unsaturated and saturated fatty acids used in the methods of the present invention are in the form of the free fatty acid and/or salt thereof. Suitable salts are alkali metal salts, such as sodium, and/or potassium; ammonium salts; and/or alkylamine salts, such as isopropylamine, am inomethylpropanol, monoethanolamine, diethanolamine, and/or triethanolamine. Alkali metal, particularly potassium, salts are preferred.

The fatty acid salts are preferably formed in situ by the addition of suitable salt forming material, e.g. base, such as sodium hydroxide, preferably potassium hydroxide, to the fatty acid containing composition. The base is preferably added as a relatively dilute aqueous solution, e.g. at a concentration of 1 to 30%, preferably 5 to 20%, more preferably about 10 to 15% w/w. The addition of base can be used to control the pH of the composition which is preferably in the range from 6 to 9, more preferably 7 to 8.5, particularly 7.2 to 8.2, and especially 7.5 to 8. A surprising improvement in the pest control properties of the composition can be achieved at these pH values.

In one embodiment, the amount of fatty acid salts in the composition is preferably in the range from 50 to 100%, more preferably 90 to 99.9%, particularly 95 to 99.5%, and especially 96 to 99% by weight, based on the total amount of fatty acids and salts thereof in the composition. Correspondingly, the amount of free fatty acids is preferably in the range from 0 to 50%, more preferably 0.1 to 10%, particularly 0.5 to 5%, and especially 1 to 4% by weight, based on the total weight of fatty acids and salts thereof in the composition.

The fatty acids and/or salts thereof are suitably present in a composition according to various methods of the present invention in the range from 3 to 50%, preferably 5 to 40%, more preferably 10 to 30%, particularly 15 to 25%, and especially 18 to 22% by weight, based on the total amount of the composition.

The unsaturated fatty acids and/or salts thereof used in the methods of the present invention comprise, consist essentially of, or consist of, in the range from 12 to 26, preferably 14 to 24, more preferably 16 to 22, particularly 18 to 20, and especially 18 carbon atoms. In one embodiment, greater than 50%, preferably greater than 60%, more preferably greater than 70%, particularly greater than 80%, and especially greater than 90% and up to 100% by weight of the unsaturated fatty acids fall within one or more of the above carbon atom ranges, based on the total weight of unsaturated fatty acids in the composition.

Suitable unsaturated fatty acids are selected from the group consisting of oleic, elaidic, ricinoleic, dodecenoic, tetradecenoic (myristoleic), hexadecenoic (palm itoleic), octadecadienoic (linoleic or linolelaidic), octadecatrienoic (linolenic), eicosenoic (gadoleic), eicosatetraenoic (arachidonic), docosenoic (erucic), docosenoic (brassidic), docosapentaenoic (clupanodonic), eicosapentaenoic, docosahexaenoic, gamma-linolenic, dihomo-gamma-linolenic, arachidonic, acids, and mixtures thereof. Preferred unsaturated fatty acids are selected from the group consisting of oleic, ricinoleic, linoleic, linolenic, acids and mixtures thereof. Particularly preferred unsaturated fatty acids are selected from the group consisting of oleic, ricinoleic, linoleic, acids and mixtures thereof.

The unsaturated fatty acids are preferably monocarboxylic acids and may be linear or branched, and are preferably linear. The unsaturated fatty acids may be in the form of cis and/or trans isomers. Oleic acid is a preferred cis isomer, and elaidic acid a preferred trans isomer. The unsaturated fatty acids may be unsubstituted, or substituted, for example with one or more hydroxyl groups. Ricinoleic acid is a preferred hydroxy acid.

The unsaturated fatty acids may be mono-unsaturated, di-unsaturated or polyunsaturated, i.e. containing one, two or more than two carbon-carbon double bonds respectively. Oleic acid is a preferred mono-unsaturated fatty acid, and linoleic acid is a preferred di-unsaturated fatty acid. In one embodiment, the concentration of (i) mono-unsaturated fatty acids is preferably greater than 10%, more preferably greater than 20%, and particularly in the range from 30 to 90%, by weight, (ii) di-unsaturated fatty acids is preferably greater than 5%, more preferably greater than 10%, and particularly in the range from 15 to 50% by weight, (iii) mono-unsaturated and di-unsaturated fatty acids combined is preferably greater than 75%, more preferably greater than 85%, particularly greater than 90%, and especially in the range from 95 to 100% by weight, and/or (iv) polyunsaturated fatty acids is preferably less than 25%, more preferably less than 15%, particularly less than 5%, and especially in the range from 0 to 3% by weight, all based on the total weight of unsaturated fatty acids in the composition.

The concentration of unsaturated fatty acids and/or salts thereof present in a composition useful in the methods of the present invention is suitably in the range from 10 to 90%, preferably 20 to 80%, more preferably 30 to 70%, particularly 40 to 60%, and especially 45 to 55% by weight, based on the total weight of fatty acids and/or salts thereof in the composition.

In certain compositions useful in an embodiment of the present invention, the unsaturated fatty acids used in various methods of the invention comprise a mixture of unsubstituted fatty acids and hydroxy fatty acids, preferably present at a ratio of 10 to 90%:10 to 90%, more preferably 30 to 70%:30 to 70%, particularly 40 to 60%:40 to 60%, and especially 45 to 55%:45 to 55% by weight, based on the total weight of unsaturated fatty acids in the composition. A particularly preferred combination is a mixture of oleic acid and ricinoleic acid.

The saturated fatty acids and/or salts thereof used in various methods of the present invention comprise, consist essentially of, or consist of, in the range from 6 to 14, preferably 6 to 12, more preferably 8 to 12, and particularly 8 to 10 carbon atoms. In one embodiment, greater than 50%, preferably greater than 60%, more preferably greater than 70%, particularly greater than 80%, and especially greater than 90% and up to 100% by weight of the saturated fatty acids fall within one or more of the above carbon atom ranges, based on the total weight of saturated fatty acids in the composition.

The saturated fatty acids are preferably monocarboxylic acids and may be linear and/or branched, and are preferably linear.

Suitable saturated fatty acids are selected from the group consisting of hexanoic (caproic), octanoic (caprylic), nonanoic, decanoic (capric), undecanoic, dodecanoic (lauric), tridecanoic, tetradecanoic acid (myristic), 2-ethyl hexanoic, trimethylhexanoic, trimethylnonanoic, acids and mixtures thereof. Preferred saturated fatty acids are selected from the group consisting of caprylic, capric, 2-ethyl hexanoic, trimethylhexanoic, trimethylnonanoic, tetramethylhexanoic, acids, and mixtures thereof. Particularly preferred saturated fatty acids are selected from the group consisting of caprylic, capric, 2-ethyl hexanoic, trimethylhexanoic, acids, and mixtures thereof.

Lauric acid is a saturated fatty acid with a 12-carbon atom chain, and is found naturally in coconuts. Lauric acid is also known as dodecanoic acid.

The concentration of saturated fatty acids and/or salts thereof present in a composition according to methods of the present invention is suitably in the range from 10 to 90%, preferably 20 to 80%, more preferably 30 to 70%, particularly 40 to 60%, and especially 45 to 55% by weight, based on the total weight of fatty acids and/or salts thereof in the composition.

The ratio by weight of unsaturated fatty acids and/or salts thereof to saturated fatty acids and/or salts thereof in a composition according to various methods of the present invention is preferably in the range from 0.2 to 5:1, more preferably 0.35 to 3:1, particularly 0.5 to 2:1, and especially 0.8 to 1.2:1.

In one embodiment, the mean number of carbon atoms, on a weight basis, present in the unsaturated fatty acids and/or salts is suitably at least 2, preferably at least 4, more preferably in the range from 6 to 12, particularly 7 to 11, and especially 8 to 10 carbon atoms greater than the mean number of carbon atoms present in the saturated fatty acids and/or salts. The mean number of carbon atoms by weight present in the unsaturated fatty acids and/or salts is preferably in the range from 14 to 22, more preferably 16 to 20, particularly 17 to 19, and especially 17.5 to 18.5. The mean number of carbon atoms by weight present in the saturated fatty acids and/or salts is preferably in the range from 6 to 12, more preferably 7 to 11, particularly 8 to 10, and especially 8.5 to 9.5.

In those compositions including more than one oil, each oil can make up between about 0.1%, or less, to about 99%, or more, by weight, of the composition mixture. For example, one composition of the present invention comprises about 1% thymol and about 99% geraniol. Optionally, the compositions can additionally comprise a fixed oil, which is a non-volatile non-scented plant oil. Fixed oils may stabilize the composition, limiting the evaporation of the active components. Fixed oils useful in the formulations of the present invention include, but are not limited to, castor oil, corn oil, cottonseed oil, cumin oil, linseed oil, mineral oil, white mineral oil, olive oil, peanut oil, safflower oil, sesame oil, and soybean oil.

In certain exemplary embodiments, arthropod control compositions according to the invention include at least one of geraniol, isopropyl alcohol, benzyl alcohol, butyl lactate, vanillin, isopropyl myristate, and triethyl citrate. In certain exemplary embodiments, arthropod control compositions according to the invention include at least two of geraniol, isopropyl alcohol, benzyl alcohol, butyl lactate, vanillin, isopropyl myristate, and triethyl citrate. In certain exemplary embodiments, arthropod control compositions according to the invention include geraniol, isopropyl alcohol, benzyl alcohol, butyl lactate, vanillin, isopropyl myristate, and triethyl citrate. In certain exemplary embodiments, arthropod control compositions according to the invention include geraniol, benzyl alcohol, butyl lactate, vanillin, isopropyl myristate, and triethyl citrate. In certain exemplary embodiments, arthropod control compositions according to the invention include geraniol, benzyl alcohol, butyl lactate, vanillin, and isopropyl myristate. In certain exemplary embodiments, arthropod control compositions according to the invention include geraniol, benzyl alcohol, butyl lactate, and isopropyl myristate. In certain exemplary embodiments, arthropod control compositions according to the invention include geraniol, benzyl alcohol, and isopropyl myristate.

While embodiments of the invention can include active ingredients, carriers, inert ingredients, and other formulation components, preferred embodiments begin with a primary blend. A primary blend is preferably a synergistic combination containing two or more active ingredients and, optionally, additional ingredients. The primary blends can then be combined with other ingredients to produce a formulation. Accordingly, where concentrations, concentration ranges, or amounts, are given herein, such quantities typically are in reference to a primary blend or blends. Thus, when a primary blend is further modified by addition of other ingredients to produce a formulation, the concentrations of the active ingredients are reduced proportional to the presence of other ingredients in the formulation.

In preferred blends, geraniol can be included at a concentration of between 5% or less to 50% or more; at a concentration between 10%-40%; at a concentration of about 15%; at a concentration of about 16%; at a concentration of about 19%; or at a concentration of about 26% by weight.

In preferred blends, benzyl alcohol can be included at a concentration of between 10% or less to 70% or more; at a concentration between 20%-60%; at a concentration of about 28%; at a concentration of about 30%; at a concentration of about 34%; or at a concentration of about 48% by weight.

In preferred blends, vanillin can be included at a concentration of between 2.5% or less to 20% or more; at a concentration between 3%-15%; at a concentration of about 4%; at a concentration of about 8%; or at a concentration of about 12% by weight.

In preferred blends, isopropyl myristate can be included at a concentration of between 10% or less to 50% or more; at a concentration between 10%-40%; at a concentration of about 15%; at a concentration of about 18%; at a concentration of about 25%; or at a concentration of about 30% by weight.

In preferred blends, triethyl citrate can be included at a concentration of between 9% or less to 40% or more; at a concentration between 10%-30%; at a concentration of about 10%; at a concentration of about 13%; or at a concentration of about 20% by weight.

In preferred blends, butyl lactate can be included at a concentration of between 10% or less to 50% or more; at a concentration between 20%-40%; at a concentration of about 23%; or at a concentration of about 28% by weight.

The compositions of the present invention can comprise, in admixture with one or more suitable carrier and optionally with a suitable surface active agent and/or one or more surfactant agents, plant essential oil compounds and/or derivatives thereof, natural and/or synthetic, including racemic mixtures, enantiomers, diastereomers, hydrates, salts, solvates and metabolites, etc.

A suitable carrier can include any carrier in the art known for plant essential oils, provided the carrier does not adversely affect the compositions of the present invention. The term "carrier" as used herein means an inert or fluid material, which can be inorganic or organic and of synthetic or natural origin, with which the active compound is mixed or formulated to facilitate its application to the host, area, or other object to be treated, or to facilitate its storage, transport and/or handling. In general, any of the materials customarily employed in formulating repellents, pesticides, herbicides, or fungicides, are suitable.

The compositions of the present invention can be employed alone or in the form of mixtures with such solid and/or liquid dispersible carrier vehicles and/or other known compatible active agents such as other repellents, pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

The compositions of the present invention can be formulated or mixed with, if desired, conventional inert pesticide diluents or extenders of the type usable in conventional arthropod control agents, e.g., conventional dispersible carrier vehicles such as gases, solutions, emulsions, suspensions, emulsifiable concentrates, spray powders, pastes, soluble powders, wettable powders, dusting agents, granules, foams, mousses, pastes, tablets, aerosols, amorphous silica, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

The compositions of the present invention can further comprise surface-active agents. Examples of surface-active agents that can be employed with the present invention, include emulsifying agents, such as non-ionic and/or anionic emulsifying agents (e.g., polyethylene oxide esters of fatty acids, polyethylene oxide ethers of fatty alcohols, cyclodextrins, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents such as lignin, sulfite waste liquors, methyl cellulose, etc.

In some embodiments, water-based formulations are preferred. Although oil-based formulations of arthropod control agents are generally more effective, water-based formulations have the advantage that they do not leave behind an oily residue on treated surfaces.

The surfactant of the water-based formulation is provided to facilitate mixture of the arthropod control composition with the water. The surfactant may include an end having a carboxyl group, which will face the water molecules, and a hydrocarbon end, which will face an oil component of the arthropod control composition. As such, the surfactant allows the water and the oil component of the composition to be mixed to form an emulsion. Various surfactants may be used in the formulation of the present invention, for example, sodium lauryl sulfate (SLS, anionic), chlorhexidine (CLH, cationic), and Poloxamer 407 (POL407, non-ionic), Sodium dodecylsulfate (SDS), Sodium cholate, Sodium deoxycholate, N-Lauroylsarcosine, Lauryldimethylamine-oxide (LDAO), Cetyltrimethylammoniumbromide (CTAB), Bis(2-ethylhexyl) sulfosuccinate, potassium salts of fatty acids, straight-chain alkyl benzene sulfonates, Ammonium Lauryl Sulfate, ammonium lauryl ether sulfate, or mixtures thereof.

The solvent of the water-based formulation serves to reduce the water-oil surface tension of the emulsion or composition. By reducing this surface tension, the oil spots are more readily dispersed in the water, and a thin film of the oil-water mixture is allowed to form on the treated surfaces, which surfaces may include a host, areas within a household, outdoor areas, plants and the arthropods themselves. The solvent may also serve as a carrier and a synergist. The solvent may assist in fast penetration through the cell membrane of an arthropod being controlled to ensure the arrival of sufficient active ingredients to the site of action. The solvent may assist in wetting the arthropod exoskeleton to facilitate exposure of the cell membrane to the formulation and/or may dissolve portions of the exoskeleton. The solvent is suitably relatively polar, and preferably is a lower alcohol or ester having a molecular weight of less than 400, more preferably less than 200, and particularly in the range from 40 to 100. Isopropanol and/or ethanol are particularly preferred lower alcohol cosolvents. Various solvents may be used, for example, mineral oil, white mineral oil, isopar M, isopar C, alcohol, ethanol, isopropanol, or mixtures thereof.

Table 1 shows preferred preparations and Table 2 shows preferred concentrations of the ingredients in the preparations.

TABLE 1

TyraTech preferred preparations.

| | F-4224/TT HLK | TT 0831 | TT | B-5096 | B-5062 | B-5096 propellent | B-5062 propellent | TT personal repellent |
|---|---|---|---|---|---|---|---|---|
| geraniol | x | x | x | x | x | x | x | x |
| vanillin | x | x | x | x | x | x | x | x |
| isopropyl myristate | x | x | x | x | x | x | x | x |
| triethyl citrate | x | x | x | x | x | x | x | x |
| benzyl alcohol | x | | x | | | | | |
| isopropyl alcohol | x | | x | x | x | x | x | x |
| butyl lactate | x | | x | x | x | x | x | |
| stepanol WAC | x | | x | x | x | x | x | |
| germaben 11 | x | | | | | x | x | |
| A-46 propellent | x | | | | | x | x | |
| DI water | x | | x | x | x | x | x | |
| Equate baby shampoo | | x | | | | | | |
| thyme oil white 3 | | x | x | | x | | x | |
| linalool | | x | x | | x | | x | |
| THL | | x | x | | x | | x | |
| heliotropine | | x | x | | x | | x | |
| lauric acid | | | | | | | | x |
| white mineral oil | | | | | | | | x |
| vitamin e | | | | | | | | x |

TABLE 2

Preferred concentrations.

| | | | | | | | | | Range 1 | Range 2 | Range 3 |
|---|---|---|---|---|---|---|---|---|---|---|---|
| F-4224/ TT HLK | | | | | | | | | | | |
| geraniol 0.1%-30% | 0.08 | 0.16 | 0.57 | 0.67 | 0.82 | 1.23 | 3.28 | 8.20 | .1-20 | .5-15 | 1-10 |
| vanillin 0.01%-5% | 0.02 | 0.04 | 0.13 | 0.16 | 0.19 | 0.29 | 0.76 | 1.90 | .01-4 | 0.3-2 | 1-10 |
| IPM 0.1%-30% | 0.10 | 0.16 | 0.55 | 0.65 | 0.79 | 1.19 | 3.16 | 7.90 | .1-20 | .4-10 | 1-5 |
| TEC 0.1%-30% | 0.10 | 0.14 | 0.49 | 0.57 | 0.70 | 1.05 | 2.80 | 7.00 | .1-20 | .4-10 | 1-5 |
| benzyl alcohol 0.01%-30% | 0.15 | 0.30 | 1.05 | 1.23 | 1.50 | 2.25 | 6.00 | 15.00 | .1-20 | .4-10 | 1-5 |
| isopropyl alcohol 0.1%-80% | 0.15 | 0.30 | 1.05 | 1.23 | 1.50 | 2.25 | 6.00 | 15.00 | .1-20 | .4-10 | 1-5 |
| butyl lactate 0.1%-30% | 0.13 | 0.25 | 0.88 | 1.03 | 1.25 | 1.88 | 5.00 | 12.50 | .1-20 | .4-10 | 1-5 |
| stepanol WAC 0.02%-30% | 0.05 | 0.09 | 0.32 | 0.37 | 0.45 | 0.68 | 1.80 | 4.50 | .01-10 | .04-8 | 1-5 |
| germaben II 0.001%-2% | 0.03 | 0.05 | 0.18 | 0.21 | 0.25 | 0.38 | 1.00 | 2.00 | .001-1.5 | .04-1 | .5-.8 |
| A-46 propellent 1%-20% | 0.60 | 1.20 | 4.20 | 4.92 | 6.00 | 9.00 | 20.00 | 20.00 | 1.5-20 | 2.5-15 | 4-15 |
| DI water 0%-98% | 98.60 | 97.31 | 90.59 | 88.97 | 86.55 | 79.83 | 50.20 | 6.00 | bal | bal | bal |
| TT 0831 | | | | | | | | | | | |
| geraniol 0.1%-30% | 0.11 | 0.12 | 0.23 | 0.35 | 0.59 | 0.70 | 0.94 | 1.17 | .1-20 | .5-15 | 1-10 |
| vanillin 0.01%-5% | 0.01 | 0.01 | 0.03 | 0.04 | 0.07 | 0.08 | 0.10 | 0.13 | .01-4 | 0.3-2 | 1-10 |
| IPM 0.1%-30% | 0.20 | 0.23 | 0.45 | 0.68 | 1.13 | 1.36 | 1.81 | 2.26 | .1-20 | .4-10 | 1-5 |
| TEC 0.1%-30% | 0.20 | 0.23 | 0.45 | 0.68 | 1.14 | 1.36 | 1.82 | 2.27 | .1-20 | .4-10 | 1-5 |
| isopropyl alcohol 0.1%-80% | 1.35 | 1.50 | 3.00 | 4.50 | 7.50 | 9.00 | 12.00 | 15.00 | .1-20 | .4-10 | 1-5 |
| butyl lactate 0.1%-30% | 1.13 | 1.25 | 2.50 | 3.75 | 6.25 | 7.50 | 10.00 | 12.50 | .1-20 | .4-10 | 1-5 |
| stepanol WAC 0.02%-30% | 0.41 | 0.45 | 0.90 | 1.35 | 2.25 | 2.70 | 3.60 | 4.50 | .01-10 | .04-8 | 1-5 |
| thyme oil white 3 0%-30% | 1.16 | 1.29 | 2.58 | 3.87 | 6.45 | 7.74 | 10.32 | 12.90 | 1.2-25 | 2-20 | 4-10 |
| linalool 0%-30% | 0.14 | 0.16 | 0.32 | 0.48 | 0.80 | 0.96 | 1.28 | 1.61 | .12-25 | .2-20 | .4-10 |
| THL 0%-30% | 0.20 | 0.22 | 0.44 | 0.66 | 1.10 | 1.32 | 1.76 | 2.20 | .2-25 | .4-20 | .8-10 |
| heliotropine 0.01%-15% | 0.24 | 0.27 | 0.53 | 0.80 | 1.33 | 1.60 | 2.13 | 2.66 | .04-12 | .08-9 | .12-5 |
| DI water 0%-98% | 48.47 | 47.66 | 45.25 | 42.33 | 36.49 | 33.56 | 27.72 | 21.87 | bal | bal | bal |
| shampoo base 0%-98% | 46.38 | 46.63 | 43.31 | 40.51 | 34.92 | 32.12 | 26.53 | 20.93 | bal | bal | bal |
| TT | | | | | | | | | | | |
| geraniol 0.1%-30% | 0.11 | 0.12 | 0.18 | 0.29 | 0.35 | 0.39 | 0.47 | 0.70 | .1-20 | .5-15 | 1-10 |
| vanillin 0.01%-5% | 0.01 | 0.01 | 0.02 | 0.03 | 0.04 | 0.04 | 0.05 | 0.08 | .01-4 | 0.3-2 | 1-10 |
| IPM 0.1%-30% | 0.20 | 0.23 | 0.34 | 0.57 | 0.68 | 0.75 | 0.90 | 1.36 | .1-20 | .4-10 | 1-5 |
| TEC 0.1%-30% | 0.20 | 0.23 | 0.34 | 0.57 | 0.68 | 0.75 | 0.91 | 1.36 | .1-20 | .4-10 | 1-5 |
| benzyl alcohol 0.01%-30% | 1.35 | 1.50 | 2.25 | 3.75 | 4.50 | 4.95 | 6.00 | 9.00 | .1-20 | .4-10 | 1-5 |

TABLE 2-continued

| Preferred concentrations. | | | | | | | | | Range 1 | Range 2 | Range 3 |
|---|---|---|---|---|---|---|---|---|---|---|---|
| isopropyl alcohol 0.1%-80% | 1.35 | 1.50 | 2.25 | 3.75 | 4.50 | 4.95 | 6.00 | 9.00 | .1-20 | .4-10 | 1-5 |
| butyl lactate 0.1%-30% | 1.13 | 1.25 | 1.88 | 3.13 | 3.75 | 4.13 | 5.00 | 7.50 | .1-20 | .4-10 | 1-5 |
| stepanol WAC 0.02%-30% | 0.41 | 0.45 | 0.68 | 1.13 | 1.35 | 1.49 | 1.80 | 2.70 | .01-10 | .04-8 | 1-5 |
| germaben II 0.001%-2% | 0.23 | 0.25 | 0.38 | 0.63 | 0.75 | 0.83 | 1.00 | 1.50 | .001-1.5 | .04-1 | .5-.8 |
| A-46 propellent 1%-20% | 5.40 | 6.00 | 9.00 | 15.00 | 18.00 | 19.80 | 24.00 | 36.00 | 1.5-20 | 2.5-15 | 4-15 |
| thyme oil white 30%-30% | 1.16 | 1.29 | 1.94 | 3.23 | 3.87 | 4.26 | 5.16 | 7.74 | 1.2-25 | 2-20 | 4-10 |
| linalool 0%-30% | 0.14 | 0.16 | 0.24 | 0.40 | 0.48 | 0.53 | 0.64 | 0.96 | .12-25 | .2-20 | .4-10 |
| THL 0%-30% | 0.20 | 0.22 | 0.33 | 0.55 | 0.66 | 0.73 | 0.88 | 1.32 | .2-25 | .4-20 | .8-10 |
| heliotropine 0.01%-15% | 0.24 | 0.27 | 0.40 | 0.67 | 0.80 | 0.88 | 1.06 | 1.60 | .04-12 | .08-9 | .12-5 |
| DI water 0%-98% | 87.88 | 86.53 | 79.80 | 66.33 | 59.59 | 55.55 | 46.12 | 19.18 | bal | bal | bal |
| B-5096 | | | | | | | | | | | |
| geraniol 0.1%-30% | 0.16 | 0.41 | 0.82 | 1.64 | 2.46 | 4.10 | 4.92 | 6.56 | .1-20 | .5-15 | 1-10 |
| vanillin 0.01%-5% | 0.04 | 0.10 | 0.19 | 0.38 | 0.57 | 0.95 | 1.14 | 1.52 | .01-4 | 0.3-2 | 1-10 |
| IPM 0.1%-30% | 0.16 | 0.40 | 0.79 | 1.58 | 2.37 | 3.95 | 4.74 | 6.32 | .1-20 | .4-10 | 1-5 |
| TEC 0.1%-30% | 0.14 | 0.35 | 0.70 | 1.40 | 2.10 | 3.50 | 4.20 | 5.60 | .1-20 | .4-10 | 1-5 |
| isopropyl alcohol 0.1%-80% | 0.30 | 0.75 | 1.50 | 3.00 | 4.50 | 7.50 | 9.00 | 12.00 | .1-20 | .4-10 | 1-5 |
| butyl lactate 0.1%-30% | 0.25 | 0.63 | 1.25 | 2.50 | 3.75 | 6.25 | 7.50 | 10.00 | .1-20 | .4-10 | 1-5 |
| stepanol WAC 0.02%-30% | 0.09 | 0.23 | 0.45 | 0.90 | 1.35 | 2.25 | 2.70 | 3.60 | .01-10 | .04-8 | 1-5 |
| DI water 0%-98% | 98.86 | 97.15 | 94.30 | 88.60 | 82.90 | 71.50 | 65.80 | 54.40 | bal | bal | bal |
| B-5062 | | | | | | | | | | | |
| geraniol 0.1%-30% | 0.11 | 0.12 | 0.35 | 0.59 | 0.70 | 0.82 | 1.17 | 1.40 | .1-20 | .5-15 | 1-10 |
| vanillin 0.01%-5% | 0.01 | 0.01 | 0.04 | 0.07 | 0.08 | 0.09 | 0.13 | 0.16 | .01-4 | 0.3-2 | 1-10 |
| IPM 0.1%-30% | 0.20 | 0.23 | 0.68 | 1.13 | 1.36 | 1.58 | 2.26 | 2.71 | .1-20 | .4-10 | 1-5 |
| TEC 0.1%-30% | 0.20 | 0.23 | 0.68 | 1.14 | 1.36 | 1.59 | 2.27 | 2.72 | .1-20 | .4-10 | 1-5 |
| isopropyl alcohol 0.1%-80% | 1.35 | 1.50 | 4.50 | 7.50 | 9.00 | 10.50 | 15.00 | 18.00 | .1-20 | .4-10 | 1-5 |
| butyl lactate 0.1%-30% | 1.13 | 1.25 | 3.75 | 6.25 | 7.50 | 8.75 | 12.50 | 15.00 | .1-20 | .4-10 | 1-5 |
| stepanol WAC 0.02%-30% | 0.41 | 0.45 | 1.35 | 2.25 | 2.70 | 3.15 | 4.50 | 5.40 | .01-10 | .04-8 | 1-5 |
| thyme oil white 3 0%-30% | 1.16 | 1.29 | 3.87 | 6.45 | 7.74 | 9.03 | 12.90 | 15.48 | 1.2-25 | 2-20 | 4-10 |
| linalool 0%-30% | 0.14 | 0.16 | 0.48 | 0.80 | 0.96 | 1.12 | 1.61 | 1.93 | .12-25 | .2-20 | .4-10 |
| THL 0%-30% | 0.20 | 0.22 | 0.66 | 1.10 | 1.32 | 1.54 | 2.20 | 2.64 | .2-25 | .4-20 | .8-10 |
| heliotropine 0.01%-15% | 0.24 | 0.27 | 0.80 | 1.33 | 1.60 | 1.86 | 2.66 | 3.19 | .04-12 | .08-9 | .12-5 |

TABLE 2-continued

| Preferred concentrations. | | | | | | | | | Range 1 | Range 2 | Range 3 |
|---|---|---|---|---|---|---|---|---|---|---|---|
| DI water 0%-98% | 94.85 | 94.21 | 82.84 | 71.40 | 65.68 | 59.96 | 42.81 | 31.37 | bal | bal | bal |
| B-5096 propellent | | | | | | | | | | | |
| geraniol 0.1%-30% | 0.41 | 0.66 | 0.82 | 2.46 | 3.28 | 4.10 | 5.74 | 8.20 | .1-20 | .5-15 | 1-10 |
| vanillin 0.01%-5% | 0.10 | 0.15 | 0.19 | 0.57 | 0.76 | 0.95 | 1.33 | 1.90 | .01-4 | 0.3-2 | 1-10 |
| IPM 0.1%-30% | 0.40 | 0.63 | 0.79 | 2.37 | 3.16 | 3.95 | 5.53 | 7.90 | .1-20 | .4-10 | 1-5 |
| TEC 0.1%-30% | 0.35 | 0.56 | 0.70 | 2.10 | 2.80 | 3.50 | 4.90 | 7.00 | .1-20 | .4-10 | 1-5 |
| isopropyl alcohol 0.1%-80% | 0.75 | 1.20 | 1.50 | 4.50 | 6.00 | 7.50 | 10.50 | 15.00 | .1-20 | .4-10 | 1-5 |
| butyl lactate 0.1%-30% | 0.63 | 1.00 | 1.25 | 3.75 | 5.00 | 6.25 | 8.75 | 12.50 | .1-20 | .4-10 | 1-5 |
| stepanol WAC 0.02%-30% | 0.23 | 0.36 | 0.45 | 1.35 | 1.80 | 2.25 | 3.15 | 4.50 | .01-10 | .04-8 | 1-5 |
| germaben II 0.001%-2% | 0.13 | 0.20 | 0.25 | 0.75 | 1.00 | 1.25 | 1.75 | 2.50 | .001-1.5 | .04-1 | .5-.8 |
| A-46 propellent 1%-20% | 3.00 | 4.80 | 6.00 | 18.00 | 20.00 | 20.00 | 20.00 | 20.00 | 1.5-20 | 2.5-15 | 4-15 |
| DI water 0%-98% | 94.03 | 90.44 | 88.05 | 64.15 | 56.20 | 50.25 | 38.35 | 20.50 | bal | bal | bal |
| B-5062 propellent | | | | | | | | | | | |
| geraniol 0.1%-30% | 0.11 | 0.12 | 0.23 | 0.35 | 0.59 | 0.82 | 1.17 | 1.40 | .1-20 | .5-15 | 1-10 |
| vanillin 0.01%-5% | 0.01 | 0.01 | 0.03 | 0.04 | 0.07 | 0.09 | 0.13 | 0.16 | .01-4 | 0.3-2 | 1-10 |
| IPM 0.1%-30% | 0.20 | 0.23 | 0.45 | 0.68 | 1.13 | 1.58 | 2.26 | 2.71 | .1-20 | .4-10 | 1-5 |
| TEC 0.1%-30% | 0.20 | 0.23 | 0.45 | 0.68 | 1.14 | 1.59 | 2.27 | 2.72 | .1-20 | .4-10 | 1-5 |
| isopropyl alcohol 0.1%-80% | 1.35 | 1.50 | 3.00 | 4.50 | 7.50 | 10.50 | 15.00 | 18.00 | .1-20 | .4-10 | 1-5 |
| butyl lactate 0.1%-30% | 1.13 | 1.25 | 2.50 | 3.75 | 6.25 | 8.75 | 12.50 | 15.00 | .1-20 | .4-10 | 1-5 |
| stepanol WAC 0.02%-30% | 0.41 | 0.45 | 0.90 | 1.35 | 2.25 | 3.15 | 4.50 | 5.40 | 1.01-0 | .04-8 | 1-5 |
| germaben II 0.001%-2% | 0.23 | 0.25 | 0.50 | 0.75 | 1.25 | 1.75 | 2.50 | 3.00 | .001-1.5 | .04-1 | .5-.8 |
| thyme oil white 3 0%-30% | 1.16 | 1.29 | 2.58 | 3.87 | 6.45 | 9.03 | 12.90 | 15.48 | 1.2-25 | 2-20 | 4-10 |
| linalool 0%-30% | 0.14 | 0.16 | 0.32 | 0.48 | 0.80 | 1.12 | 1.61 | 1.93 | .12-25 | .2-20 | .4-10 |
| THL 0%-30% | −0.20 | 0.22 | 0.44 | 0.66 | 1.10 | 1.54 | 2.20 | 2.64 | .2-25 | .4-20 | .8-10 |
| heliotropine 01%-15% | 0.24 | 0.27 | 0.53 | 0.80 | 1.33 | 1.86 | 2.66 | 3.19 | .04-12 | .08-9 | .12-5 |
| A-46 propellent 1%-20% | 5.40 | 6.00 | 12.00 | 18.00 | 20.00 | 20.00 | 20.00 | 20.00 | 1.5-20 | 2.5-15 | 4-15 |
| DI water 0%-98% | 89.23 | 88.03 | 76.06 | 64.09 | 50.15 | 38.21 | 20.31 | 8.37 | bal | bal | bal |
| TT personal repellent | | | | | | | | | | | |
| geraniol 0.1%-30% | 1.50 | 2.50 | 3.50 | 5.00 | 7.50 | 9.00 | 10.00 | 12.50 | .1-20 | .5-15 | 1-10 |
| vanillin 0.01%-5% | 0.75 | 1.25 | 1.75 | 2.50 | 3.75 | 4.50 | 5.00 | 6.25 | .01-4 | 0.3-2 | 1-10 |
| IPM 0.1%-30% | 3.06 | 5.10 | 7.14 | 10.20 | 15.30 | 18.36 | 20.40 | 25.50 | .1-20 | .4-10 | 1-5 |

TABLE 2-continued

Preferred concentrations.

|  |  |  |  |  |  |  |  |  | Range 1 | Range 2 | Range 3 |
|---|---|---|---|---|---|---|---|---|---|---|---|
| TEC 0.1%-30% | 2.79 | 4.65 | 6.51 | 9.30 | 13.95 | 16.74 | 18.60 | 23.25 | .1-20 | .4-10 | 1-5 |
| lauric acid 0.01%-50% | 3.00 | 5.00 | 7.00 | 10.00 | 15.00 | 18.00 | 20.00 | 25.00 | 2-40 | 5-30 | 10-20 |
| vitamin e 0%-10% | 0.30 | 0.50 | 0.70 | 1.00 | 1.50 | 1.80 | 2.00 | 2.50 | .2-8 | .5-5 | 1-3 |
| isopropyl alcohol 0.1%-80% | 29.24 | 26.73 | 24.22 | 21.00 | 14.19 | 10.43 | 7.92 | 1.65 | bal | bal | bal |
| white mineral oil 0%-98% | 59.36 | 54.27 | 49.18 | 41.00 | 28.81 | 21.17 | 16.08 | 3.35 | bal | bal | bal |

To produce the water-based formulation, the arthropod control composition containing one or more plant essential oils is mixed with water to create a slurry. The surfactant is then added to create certain embodiments of the water-based formulation. To create other embodiments of the water-based formulation, the solvent is then added. The final concentration of the arthropod control composition in the formulation may be, for example, about 10-25%. The final concentration of the surfactant in the formulation may be, for example, about 1-10%. The final concentration of the solvent in the formulation may be, for example, 0 to about 80%. Some embodiments of the present invention are characterized by rapid killing, e.g., kill-on-contact, and some embodiments are characterized by residual effects, i.e., formulation remains on treated surface affecting arthropod control for an extended period of time. In the case of the embodiment characterized by residual effects, it should be noted that the solvent-component of the formulation is not necessary. In such embodiments of the invention, the formulation includes: water, an arthropod control composition, a surfactant, and a stabilizer. Such embodiments may optionally include the solvent described herein.

Once the water-based formulation has been prepared, it may be applied to a desired host, area, or object to affect arthropod control. Once applied, it will form a thin film on the treated surfaces, adhering thereto and providing effective arthropod control. The formulation may be applied to the host, area, or object in a variety of manners known in the art, for example, the formulation may be prepared as an aerosol or trigger spray.

Certain mixtures of liquefied hydrocarbons, such as propellents A-46, A-70, or 142A may be used as propellents in embodiments of spray mixtures. Where an embodiment describes the use of one propellent, other embodiments are specifically contemplated in which the designated propellent is replaced with any of the other propellent, or a mixture of any of these propellents with each other or with the designated propellent.

In certain exemplary embodiments, the present invention encompasses a mixture of an arthropod control composition including one or more plant essential oils with a carrier. For example, embodiments of the present invention can include a carrier having a surface area, with the arthropod control composition coated on the surface area of the carrier. The carrier may be, for example, crystals, powder, dust, granules or the like, which provides an absorption surface area for the arthropod control compositions. One example of a carrier that can be used in accordance with the present invention is diatomaceous earth (DE). DE is a naturally occurring sedimentary rock that is easily crumbled into a fine powder. This powder has an abrasive feel, similar to pumice powder, and is very light, due to its high porosity. Diatomaceous earth consists of fossilized remains of diatoms, a type of hard-shelled algae.

To produce certain embodiments of the present invention, the carrier and the arthropod control composition are mixed to allow the carrier to become coated with the composition.

In some embodiments of the invention, after the carrier has been coated with the arthropod control composition to form the formulation, the formulation can be applied to a desired host, area, or object to affect arthropod control. Because the carrier reduces the volatility of the arthropod control composition, the composition will remain active for an amount of time that is greater than the time the composition, alone, i.e., unformulated composition, would remain active. As such, the formulation continues to provide arthropod control after the time by which the composition, alone, would have volatilized.

Embodiments of the present invention can be used to control arthropods by treating an area directly. For example, the area can be treated by spreading or dispersing the formulation, for example, manually, automatically, with a fertilizer spreader, or the like.

An area can be treated with a composition of the present invention, for example, by using a spray formulation, such as an aerosol or a pump spray, or a burning formulation, such as a candle or a piece of incense containing the composition. Of course, various treatment methods can be used without departing from the spirit and scope of the present invention. For example, compositions can be comprised in household products such as: air fresheners (including heated air fresheners in which arthropod repellent substances are released upon heating, e.g., electrically, or by burning); hard surface cleaners; or laundry products (e.g., laundry detergent-containing compositions, conditioners).

In certain embodiments of the invention, an area can be treated with a composition of the present invention, for example, by using a spray formulation, such as an aerosol or a pump spray, or a burning formulation, such as a candle or a piece of incense containing the composition, or the like. In certain embodiments of the invention, an area can be treated, for example, via aerial delivery, by truck-mounted equipment, or the like. Of course, various treatment methods can be used without departing from the spirit and scope of the present invention. For example, compositions can be comprised in household products, for example, hard surface cleaners, and the like.

An exemplary dispenser of a system of the present invention can deliver a pest control composition to the atmosphere in a continuous manner over a period of time. The exemplary dispenser can include a reservoir for holding a pest control composition, and a wick for drawing the composition from the reservoir and releasing the arthropod control composition into the atmosphere. The reservoir can be constructed from a material that is impermeable to the pest control composition, for example, appropriate glass, ceramic, or polymeric materials can be used. The reservoir can include an aperture, which can be sealed or unsealed, as desired. When the exemplary system of the present invention is not in use, the aperture can be sealed to prevent the release of the pest control composition into the atmosphere. It may be desirable, for example, to seal the aperture when the exemplary system is being stored or transported. When the system is in use, the aperture is unsealed, such that the wick can draw the pest control composition from the reservoir, and release the control composition through the aperture into the atmosphere.

In certain embodiments of the invention, the rate of release of the composition can be controlled, for example, by making adjustments to the wick of the dispenser. For example, the surface area of the wick that is exposed to the atmosphere can be altered. Generally, the greater the exposed surface area, the greater the rate of release of the pest control composition. In this regard, in certain embodiments, the dispenser can include multiple wicks and the reservoir can include multiple apertures through which the arthropod control composition can be released into the atmosphere. As another example, the wick can be constructed from a particular material that draws the pest control composition from the reservoir and releases it into the environment at a desired rate, such as, for example, a wick made of wood, a wick made of a synthetic fiber, or the like.

Another exemplary dispenser of a system of the present invention can deliver an arthropod control composition to a desired area. The dispenser can include a sealed pouch that can be constructed from a material that is impermeable to the arthropod control composition, for example, a metallic foil, a polymeric material, or the like. The pouch can define a volume for holding the arthropod control composition. The composition can be provided in a material disposed within the volume of the pouch, for example, a sponge, a cloth saturated with the material, or the like. When it becomes desirable to place the exemplary system into use, the pouch can be unsealed, exposing the composition for release into the atmosphere or for application to a desired area.

In certain embodiments the arthropod control composition is provided in a saturated cloth within the pouch, which can be used to apply the control composition a desired area. For example, a desired area can be an animal, such as a human, a domestic animal, surfaces within a dwelling, an outdoor living area, or the like.

In certain embodiments the arthropod control composition is provided in a concentrate that may be, for example, tank mixed. In certain embodiments the arthropod control composition is provided in a pouch that can be mixed with water and other adjuvants.

In certain embodiments, the dispenser can further include a hook, allowing the pouch and exposed control composition to be hung in a desired location, such as in a closet or a pantry.

In certain embodiments, a method of the present invention can deliver an arthropod control composition to a desired area. In certain embodiments, a dispenser used with the method can be constructed from a substantially planar, integral piece of material, having a first side that is coated with control composition, and a second side that is not coated with control composition. The integral piece of material can be folded and sealed such that the side coated with the control composition is contained within the volume defined by the sealed pouch. When the pouch is unsealed, the side that is coated with control composition is exposed. The substantially planar piece of material can be placed in a desired location to deliver control composition to the atmosphere, or to crawling arthropods that walk across the material.

Another exemplary dispenser of a system of the present invention can deliver an arthropod control composition to a desired area. The control composition can be incorporated into an appropriate material. In certain embodiments, the composition-containing material can be a material that is capable of controlling the release rate of the control composition, i.e., controlled-release material, allowing the control composition to be released into the atmosphere at a desired rate that can be adjusted by providing controlled-release material having appropriate specifications. The controlled-release material can be constructed from an appropriate polymer. In other embodiments the composition-containing material does not allow the control composition to be released into the atmosphere, but rather retains the control composition. An optional casing that is impermeable to the arthropod control composition can be provided to hold the composition-containing material until the system is ready for use. When the system is ready for use, the casing can be peeled away, exposing the composition-containing material. The composition-containing material can be placed in a desired location to deliver control composition to crawling arthropods that walk across the material, or to deliver the control composition to the atmosphere when a controlled-release material is used, e.g., control flying arthropods.

In certain embodiments, the composition-containing material can have a substantially planar design, appropriate for positioning adjacent a mattress for controlling lice or bed bugs, e.g., *Cimex lectularius*. A substantially planar design can also be used, for example, as or with a picnic table cloth. In certain embodiments, the composition-containing material can be used as ground cover for a garden bed or adjacent crop plants to control weeds. In certain embodiments, the composition-containing material can take the shape of a bag, and could be used for trash collection, while controlling arthropods commonly attracted to household garbage or other trash.

Another exemplary dispenser of a system of the present invention can be a substantially dry sheet containing the control composition, which control composition can be applied to a desired location upon exposing the cloth to water or an aqueous liquid, e.g., perspiration. In certain embodiments, the dry sheet containing the control composition can dissolve into a cream or gel when exposed to water or an aqueous liquid, which can then be applied to a desired area. For example, a desired area can be an animal, such as a human, a domestic animal, or another animal.

The compositions of the present invention can be used to control arthropods by either treating a host directly, or treating an area in which the host will be located. For example, the host can be treated directly by using a cream or spray formulation, which can be applied externally or topically, e.g., to the skin of a human. A composition can be applied to the host, for example, in the case of a human, using formulations of a variety of personal products or cosmetics for use on the skin or hair. For example, any of the following can be used: fragrances, colorants, pigments, dyes, colognes, skin creams, skin lotions, deodorants, talcs, bath oils, soaps, shampoos, hair conditioners, mousses, and styling agents.

In certain embodiments, the arthropod control composition is provided as a foam or mousse that is applied to the skin or hair of a host. A foam or mousse maintains the homogeneity of the formulation, reducing the separation that might occur with liquids, which may increase bioavailability of actives. It has been found that the mousse formulation makes lice and nit removal much easier. Personal observations by the clinical study PI (principal investigator) suggest the TyraTech formulation may be causing a "flushing action" of the lice i.e. immediately after the treatment is applied, the affected lice appear to quickly move to the outer portions of the hair to die rather than staying near the scalp. This "flushing action" is unexpected and contrary to a louse's typical biological behavior. Typically a louse would migrate toward the scalp to avoid light and to achieve additional purchase against the scalp and base of the hair follicles.

The present invention comprises compositions for controlling arthropods and methods for using these compositions. The present invention comprises compositions for controlling arthropods, which comprise one or more plant essential oils and methods for using these compositions. In those compositions including more than one oil, each oil can make up between about 0.1% to about 99%, by weight, of the composition mixture. For example, one composition of the present invention comprises about 1% thymol and about 99% geraniol. The plant essential oils, when combined, can have a synergistic effect. The compositions of the present invention can include any of the following oils listed below, or mixtures thereof:

| | | |
|---|---|---|
| trans-anethole | lime oil | piperonyl |
| Black seed oil (BSO) | d-limonene | piperonyl acetate |
| camphene | linalyl anthranilate | piperonyl alcohol |
| catnip oil | linalool | piperonyl amine quinone |
| carvacrol | lindenol | sabinene |
| d-carvone | methyl citrate | α-terpinene |
| 1-carvone | methyl di- | terpinene 900 |
| 1,8-cineole | hydrojasmonate | α-terpineol |
| p-cymene | myrcene | gamma-terpineol |
| dodecanoic acid | perillyl alcohol | 2-tert-butyl-p-quinone |
| diethyl phthalate | phenyl acetaldehyde | α-thujone |
| eugenol | phenylethyl alcohol | thyme oil |
| geraniol | phenylethyl propionate | thymol |
| isopropyl citrate | α-pinene | white pepper |
| lauric acid | β-pinene | wintergreen oil |
| lemon grass oil | piperine | Nootkatone |
| lilac flower oil (LFO) | piperonal | |

The compositions of the present invention may also include any of the following oils listed below, or mixtures thereof:

| | | |
|---|---|---|
| Allyl sulfide | a-farnesene | 1-octanol |
| Allyl trisulfide | (Z,E)-α-farnesene | E ocimenone |
| Allyl-disulfide | E-β-farnesene | Z ocimenone |
| Anethole | Fenchone | 3-octanone |
| t-anethole | Forskolin | Ocimene |
| Artemisia alcohol acetate | Furanodiene | Octyl acetate |
| Benzaldehyde | Furanoeudesma-1,3- | PD 98059 |
| Benzoic acid | diene | Peanut oil |
| Benzyl acetate | Furanoeudesma-1,4- | Perillyl alcohol |
| Benzyl alcohol | diene | Peppermint oil |
| Bergamotene | Furano germacra | Permethrin |
| β-bisabolene | 1,10(15)-diene-6-one | α-phellandrene |
| Bisabolene oxide | Furanosesquiterpene | β-phellandrene |
| α-bisabolol | Garlic oil | Phenethyl propionate |
| Bisabolol oxide | Geraniol | Phenyl acetaldehyde |
| Bisobolol oxide β | Geraniol acetate | Piperonal |
| Bornyl acetate | Germacrene D | Piperonyl |
| β-bourbonene | Germacrene B | Piperonyl acetate |
| Butyl lactate | Grapefruit oil | Piperonyl alcohol |
| Black seed oil | α-gurjunene | Piperonyl amine |
| α-cadinol | α-humulene | α-pinene |
| Camphene | α-ionone | β-pinene |
| α-campholene | β-ionone | Pine oil |
| α-campholene aldehyde | Isoborneol | Trans-pinocarveol |
| camphor | Isofuranogermacrene | Prenal |
| carvacrol | Iso-menthone | Propargite |
| d-carvone | Isopropanol | Pulegone |
| 1-carvone | Isopropyl alcohol | Pyrethrum |
| trans-caryophyllene | Isopropyl Myristate | Quinine |
| castor oil | Isopropyl citrate | Rosemary oil |
| cedar oil | Iso-pulegone | Sabinene |
| carbaryl | Jasinone | Sabinyl acetate |
| 1,8-cineole | cis-jasmone | Safflower oil |
| Caryophyllene oxide | Lanolin | α-santalene |
| Chamazulene | Lauric acid | Santalol |
| Chrysanthemate ester | Lavandustin A | Sativen |
| Chrysanthemic acid | Lecithin | δ-selinene |
| Chrysanthemyl alcohol | Lemon oil | β-sesquphelandrene |
| Cinnamaldehyde | Lemon grass oil | Silicone fluid |
| cinnamyl alcohol | Lilac flower oil | Sodium dodecyl sulfate |
| Cinnamon bark oil | Limonene | Soybean oil |
| Cinnamon leaf oil | d-limonene | Spathulenol |
| Cis-verbenol | Linalool | Tagetone |
| Citral A | Linalyl acetate | Tangerine oil |
| Citral B | Linalyl anthranilate | Tamoxifen |
| Citronellal | Lindestrene | Tebufenozide |
| Citronella oil | Lindenol | α-terpinene |
| Citronellol | Linseed oil | Terpinene 900 |
| Citronellyl acetate | Methyl-allyl-trisulfide | α-terpineol |
| Citronellyl formate | Menthol | α-terpinolene |
| Clove oil | 2-methoxy furanodiene | Gamma-terpineol |
| a-copaene | menthone | α-terpinyl acetate |
| cornmint oil | Menthyl acetate | tetrahydrofurfuryl |
| Corn oil | Methyl acetate | alcohol |
| β-costol | Methyl salicylate | α-thujone |
| Cryptone | Methyl cinnamate | Thyme oil |
| Curzerenone | Mint | Thymol |
| Cumin oil | p-cymene | Thymyl methyl ether |
| d-Carvone | Mineral oil | Tocopherol |
| l-Carvone | Musk abrette | Trans-caryophyllene |
| Davanone | Myrcene | Trans-pinocarveol |
| Diallyl tetrasulfide | Nepetalactone | Trans-verbenol |
| diethyl phthalate | Menthyl salicylate | Cis-verbenol |
| Dihydropyrocurzerenone | Myrtenal | Triethyl Citrate |
| Dihydrotagentone | Neraldimethyl acetate | Valeric anhydride |
| Vitamin E | Nerolidol | Vanillin |
| Nootkatone | Nonanone | Verbenone |
| Dodecanoic acid | Gamma-nonalactone | White Mineral Oil |
| β-elemene | Oil of pennyroyal | Yomogi alcohol |
| gamma-elemene | Olive oil | Zingiberene |
| Elmol | Orange sweet oil | Catnip oil |
| Estragole | Orange oil | Catmint oil |
| 2-ethyl-2-hexen-l-ol | | |
| Eugenol acetate | | |
| Eugenol | | |

Optionally, the compositions can additionally comprise a fixed oil, which is a non-volatile non-scented plant oil. For example, the composition could include one or more of the following fixed oils listed below:

| | | |
|---|---|---|
| castor oil | linseed oil | safflower oil |
| corn oil | mineral oil | sesame oil |
| cottonseed oil | olive oil | soybean oil |
| cumin oil | peanut oil | |

In some embodiments of the compositions, it can be desirable to include compounds each having a purity of about 60%, 65%, 70%, 75%, 80%, 85%, 90%, or 95%. For example, in some embodiments of the compositions that include geraniol, it can be desirable to include a geraniol that is at least about 60%, 85% or 95% pure. In some embodiments, it can be desirable to include a specific type of geraniol. For example, in some embodiments, the compositions can include: geraniol 60, geraniol 85, or geraniol 95. When geraniol is obtained as geraniol 60, geraniol 85, or geraniol 95, then forty percent, fifteen percent, or five percent of the oil can be Nerol. Nerol is a monoterpene ($C_{10}H_{18}O$), that can be extracted from attar of roses, oil of orange blossoms and oil of lavender. Embodiments of the present invention can include art-recognized ingredients normally used in such formulations. These ingredients can include, for example, antifoaming agents, anti-microbial agents, anti-oxidants, anti-redeposition agents, bleaches, colorants, emulsifiers, enzymes, fats, fluorescent materials, fungicides, hydrotropes, moisturizers, optical brighteners, perfume carriers, perfume, preservatives, proteins, silicones, soil release agents, solubilizers, sugar derivatives, sun screens, surfactants, vitamins, waxes, and the like.

In certain embodiments, embodiments of the present invention can also contain other adjuvants or modifiers such as one or more therapeutically or cosmetically active ingredients. Exemplary therapeutic or cosmetically active ingredients useful in the compositions of the invention can include, for example, fungicides, sunscreening agents, sunblocking agents, vitamins, tanning agents, plant extracts, anti-inflammatory agents, anti-oxidants, radical scavenging agents, retinoids, alpha-hydroxy acids, emollients (such as adipic acid), antiseptics, antibiotics, antibacterial agents, antihistamines, and the like, and can be present in an amount effective for achieving the therapeutic or cosmetic result desired.

In some embodiments, compositions of this invention can include one or more materials that can function as an antioxidant, such as reducing agents and free radical scavengers. Suitable materials that can function as an antioxidant can include, for example: acetyl cysteine, ascorbic acid, t-butyl hydroquinone, cysteine, diamylhydroquinone, erythorbic acid, ferulic acid, hydroquinone, p-hydroxyanisole, hydroxylamine sulfate, magnesium ascorbate, magnesium ascorbyl phosphate, octocrylene, phloroglucinol, potassium ascorbyl tocopheryl phosphate, potassium sulfite, rutin, sodium ascorbate, sodium sulfite, sodium thloglycolate, thiodiglycol, thiodiglycolamide, thioglycolic acid, thiosalicylic acid, tocopherol, tocopheryl acetate, tocopheryl linoleate, tris(nonylpheny)phosphite, and the like.

Embodiments of the invention can also include one or more materials that can function as a chelating agent to complex with metallic ions. This action can help to inactivate the metallic ions for the purpose of preventing their adverse effects on the stability or appearance of a formulated composition. Chelating agents suitable for use in an embodiment of this invention can include, for example, aminotrimethylene phosphonic acid, beta-alanine diacetic acid, calcium disodium EDTA, citric acid, cyclodextrin, cyclohexanediamine tetraacetic acid, diammonium citrate, diammonium EDTA, dipotassium EDTA, disodium azacycloheptane diphosphonate, disodium EDTA, disodium pyrophosphate, EDTA (ethylene diamine tetra acetic acid), gluconic acid, HEDTA (hydroxyethyl ethylene diamine triacetic acid), methyl cyclodextrin, pentapotassium triphosphate, pentasodium aminotrimethylene phosphonate, pentasodium triphosphate, pentetic acid, phytic acid, potassium citrate, potassium gluconate, sodium citrate, sodium diethylenetriamine pentamethylene phosphonate, sodium dihydroxyethylglycinate, sodium gluconate, sodium metaphosphate, sodium metasilicate, sodium phytate, triethanolamine ("TEA")-EDTA, TEA-polyphosphate, tetrahydroxypropyl ethylenediamine, tetrapotassium pyrophosphate, tetrasodium EDTA, tetrasodium pyrophosphate, tripotassium EDTA, trisodium EDTA, trisodium HEDTA, trisodium phosphate, and the like.

Embodiments of the invention can also include one or more materials that can function as a foaming agent, a stabilizer, a viscosity booster, or provide other useful and/or beneficial properties. Such agents suitable for use in an embodiment of this invention can include, for example, cocamide DEA, cocamide MEA, cocamide TEA, PEG-5 cocamide, PEG 20, PEG 80 cocamidopropyl betaine, ammonium xylenesulfonate, Glycerol stearate, Glycerol distearate, Sodium chloride, ammonium chloride, glycerine, propylene glycol, modified cellulose based thickeners, DMDM hydantoin, imidazolidinyl urea, isothiazolinone, methylisothiazolinone, methylchloroisothiazolinone, Sodium benzoate, 2-bromo-2-nitropropane-1,3-diol, citric acid, sodium citrate, silicone oils such as dimethicone and cyclome, panthenol, Long chain fatty alcohols like cetyl alcohol, oleyl alcohol and stearyl alcohol, stearalkonium chloride, disteardimonium chloride, quaternium-5, quaternium-15, quaternium-18, polyquaternium-10, cetrimonium chloride, isopropyl palm itate, Methylisothiazolinone, ketoconazole, zinc pyrithione, selenium sulfide, salicylate derivatives, dyes, coloring agents, polyethoxylated synthetic glycolipids, polyethoxylated synthetic monoglycerides, oatmeal, hydrocortisone, Aloe Vera, pramoxine hydrochloride, menthol, diphenhydramine, sulfur, salicylic acid, selenium sulfide, benzoyl peroxide, chlorhexidine, povidone iodine, triclosan, ethyl lactate, lecithin, paraben, methylparaben, propylparaben, lanolin, Behentrimonium Chloride, and laureth-4.

Embodiments of the invention can also include one or more materials that can function as a humectant. A humectant is added to a composition to retard moisture loss during use, which effect is accomplished, in general, by the presence therein of hygroscopic materials.

In some other embodiments, each compound can make up between about 1% to about 99%, by weight (wt/wt %) or by volume (vol/vol %), of the composition. For example, one composition of the present invention comprises about 0.821% geraniol, about 0.794% isopropyl myristate, and about 1.5% benzyl alcohol. As used herein, percent amounts, by weight or by volume, of compounds are to be understood as referring to relative amounts of the compounds. As such, for example, a composition including 7% linalool, 35% thymol, 4% alpha-pinene, 30% para-cymene, and 24% soy bean oil (vol/vol %) can be said to include a ratio of 7 to 35 to 4 to 30 to 24 linalool, thymol, alpha-pinene, para-cymene, and soybean oil, respectively (by volume). As such, if one compound is removed from the composition, or additional compounds or other ingredients are added to the composition, it is contemplated that the remaining compounds can be provided in the same relative amounts. For example, if soybean oil were removed from the exemplary composition, the resulting composition would include 7 to 35 to 4 to 40 linalool, thymol, alpha-pinene, and para-cymene, respectively (by volume). This resulting composition would include 9.21% linalool, 46.05% thymol, 5.26% alpha-pinene, and 39.48% para-cymene (vol/vol %). For another example, if safflower oil were added to the original composition to yield a final composition containing 40% (vol/vol) safflower oil, then the resulting composition would include 4.2% linalool, 21% thymol, 2.4% alpha-pinene, 18% para-cymene, 14.4% soy bean oil, and 40% safflower oil (vol/vol %). One having ordinary skill in the art would understand that volume percentages are easily converted to weight percentages based on the known or measured specific gravity of the substance.

In certain embodiments, it can be desirable to include a naturally-occurring version or a synthetic version of a compound. In certain exemplary compositions, it can be desirable to include a compound that is designated as meeting Food Chemical Codex (FCC), for example, Geraniol Fine FCC or Tetrahydrolinalool FCC, which compounds can be obtained, for example, from Renessenz LLC.

In certain embodiments, it can be desirable to combine an arthropod control blend as described herein with a synthetic insecticide such as pyrethroid compound, a nitroguanidine compound or a chloronicotinyl compound. For example, in certain embodiments it can be desirable to combine a blend with delatamethrin, clothianidin or imidacloprid, or a combination thereof. Delatamethrin is available for example from AgrEvo Environmental Health, Inc., of Montvale, N.J. Clothianidin and imidacloprid are available from Bayer CropScience LP of Research Triangle Park, N.C.

In embodiments of the invention that include at least one blend of compounds of a plant origin, the compounds of plant origin can be tested for their precise chemical composition using, for example, High-Pressure Liquid Chromatography (HPLC), Mass Spectrometry (MS), gas chromatography, or the like.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "substantially," as used herein, means at least about 80%, preferably at least about 90%, more preferably at least about 99%, for example at least about 99.9%. In some embodiments, the term "substantially" can mean completely, or about 100%.

Embodiments of the invention can include at least one oil, such as, for example, "Superior oil," highly-refined oils, and the like.

"Disablement" is an effect wherein arthropods are mobility-impaired such that their mobility is reduced as compared to arthropods that have not been exposed to the composition. In some embodiments, disablement is an effect wherein at least about 75% of arthropods are mobility-impaired such that their mobility is reduced as compared to arthropods that have not been exposed to the composition. In some embodiments, disablement is an effect wherein at least about 90% of arthropods are mobility-impaired such that their mobility is reduced as compared to arthropods that have not been exposed to the composition. In some embodiments, disablement can be caused by a disabling effect at the cellular or whole-organism level.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention. Table 3 identifies the compounds found in the experimental compositions that will be further described in the following Examples.

TABLE 3

Ingredients of Compositions used in Examples.

Figure 2:
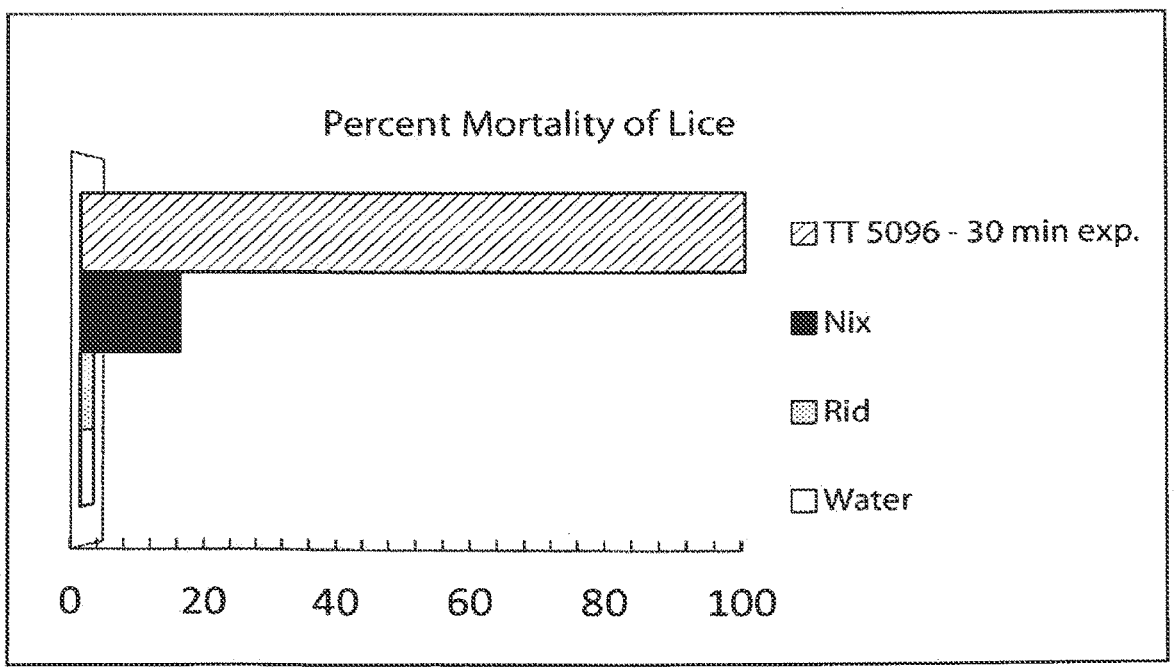
FIG. 2 shows the percent mortality of lice 4 hours after treatment with various compositions.
Figure 3:
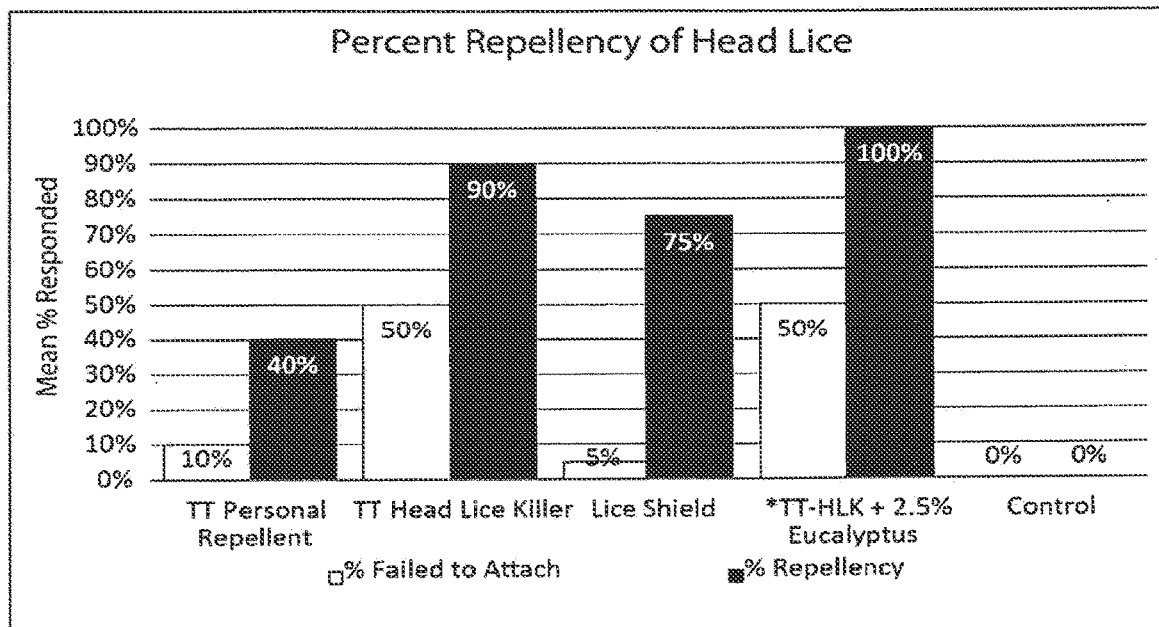
FIG. 3 shows repellency of various compositions against lice.
Figure 4:
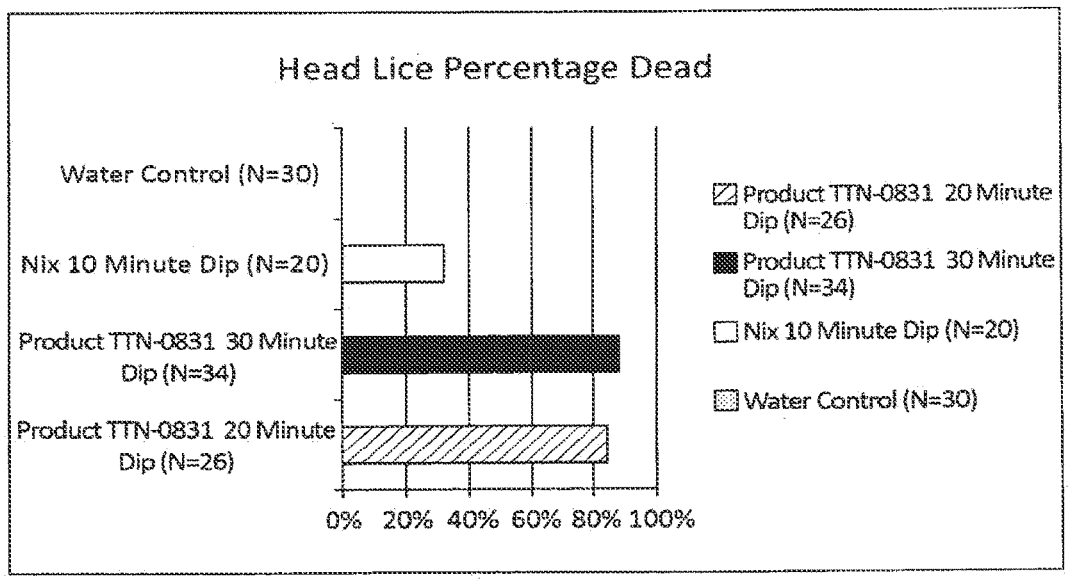
FIG. 4 shows the percent mortality of lice after treatment with various compositions
Figure 5:
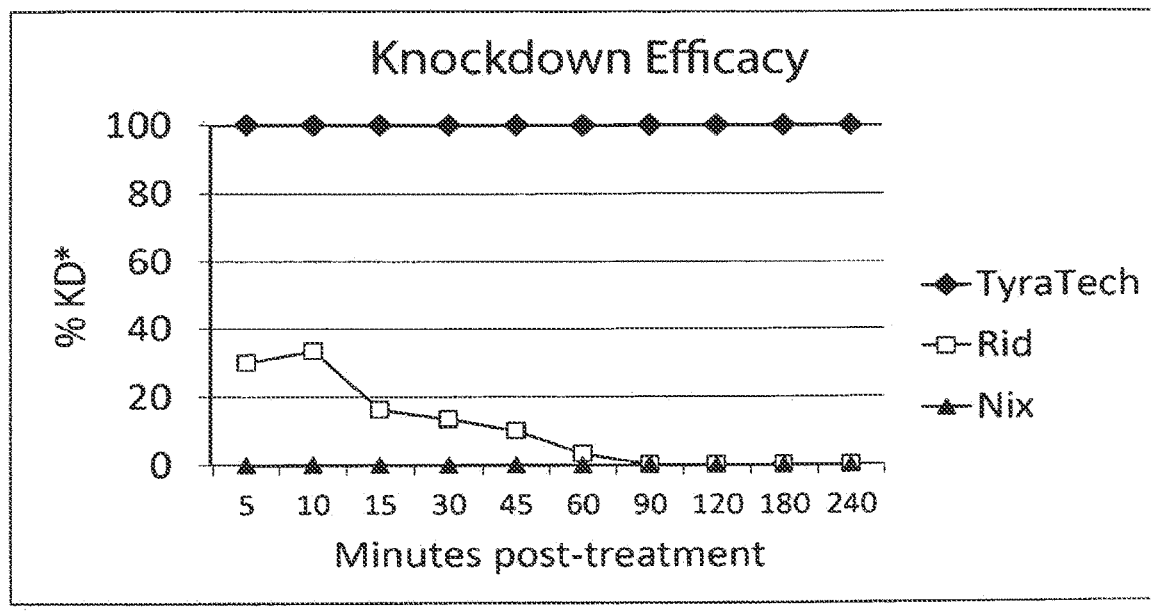
FIG. 5 shows knockdown efficacy of TyraTech formulation, RID®, or NIX® against lice in vitro.
Figure 9:
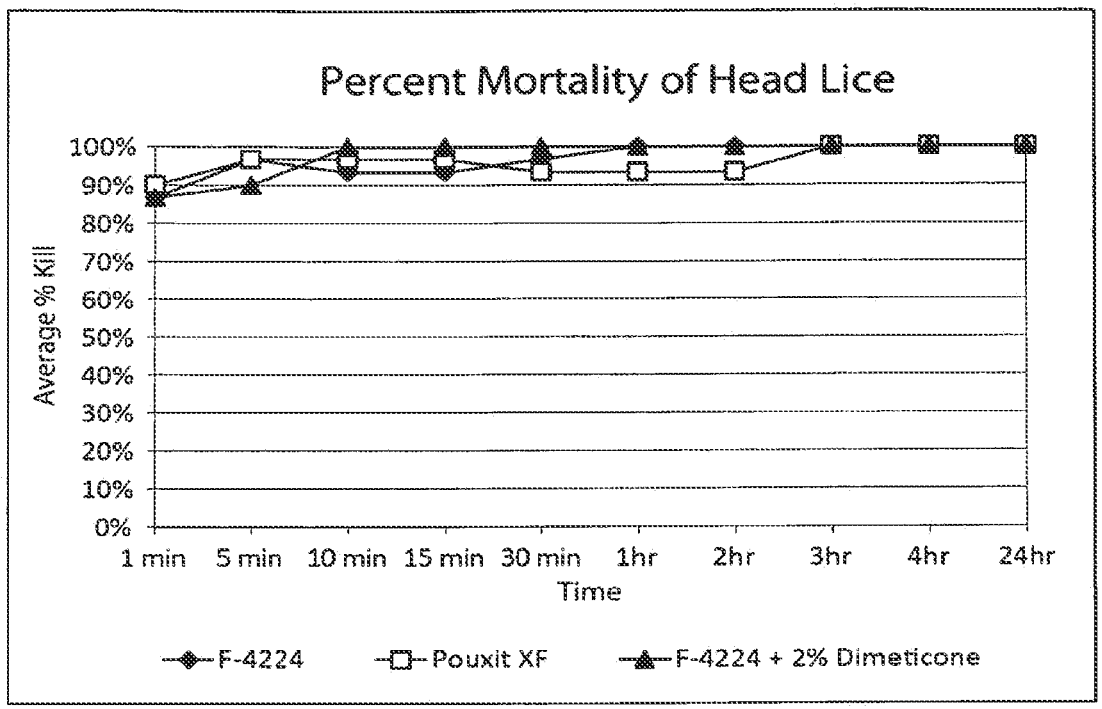
FIG. 9 shows the mortality efficacy of a 5 minute exposure of various compositions against head lice. In vitro dip method.
Figure 10:
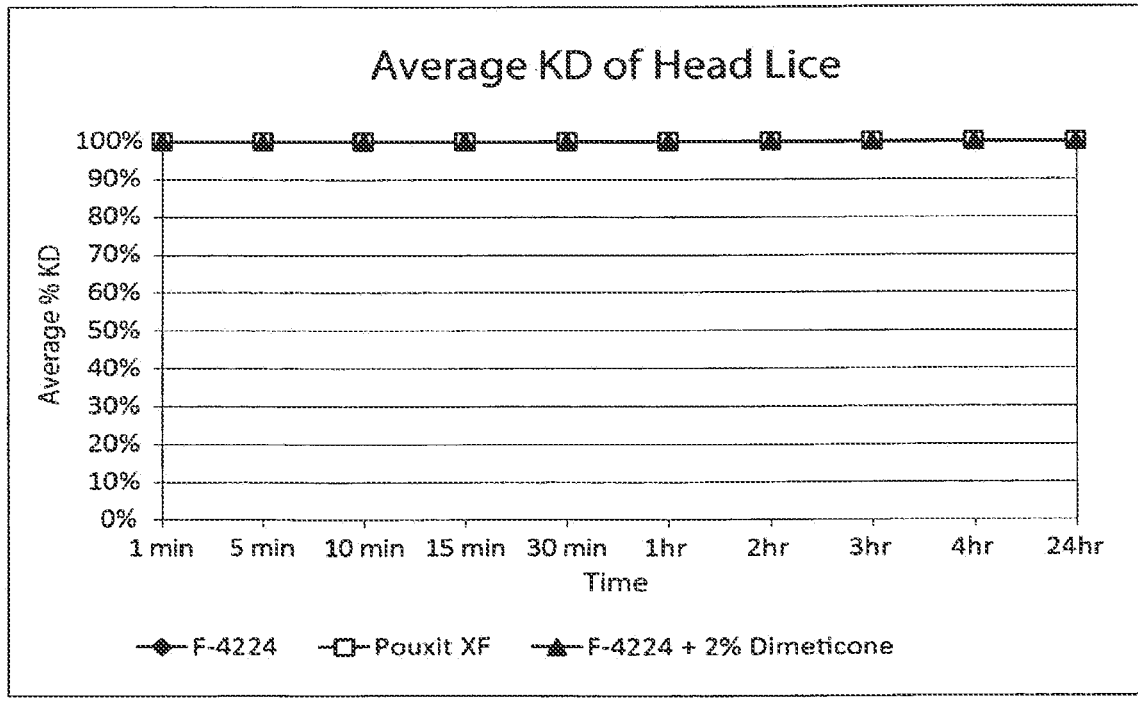
FIG. 10 shows the knockdown efficacy of a 5 minute exposure of various compositions against head lice. In vitro dip method.
Figure 11:
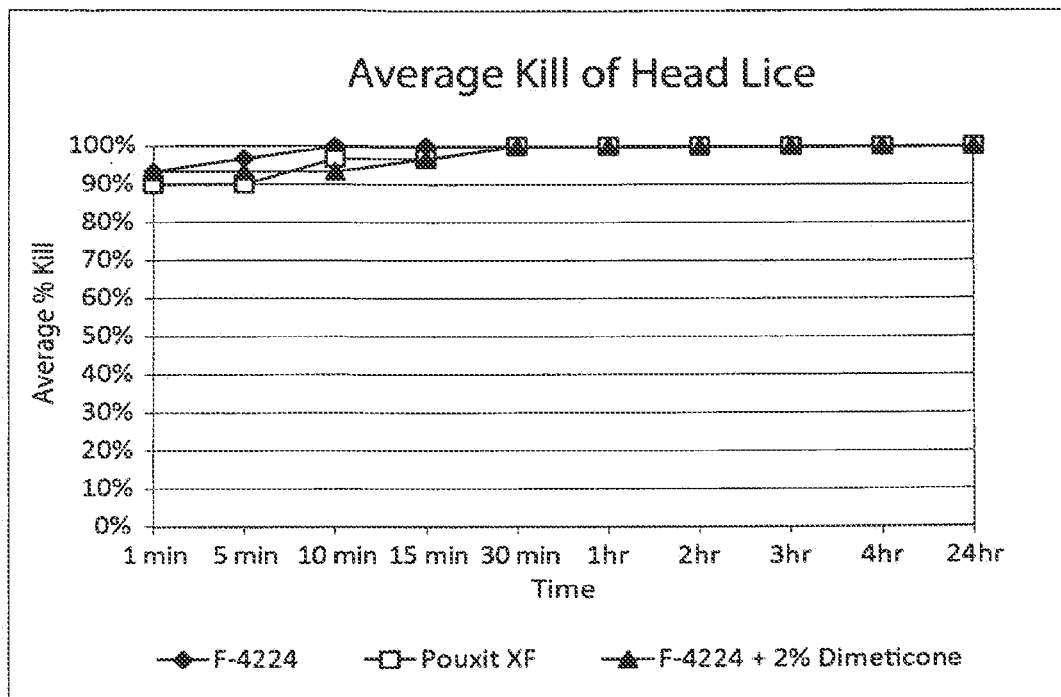
FIG. 11 shows the mortality efficacy of a 10 minutes exposure of various compositions against head lice. In vitro dip method.
Figure 12:
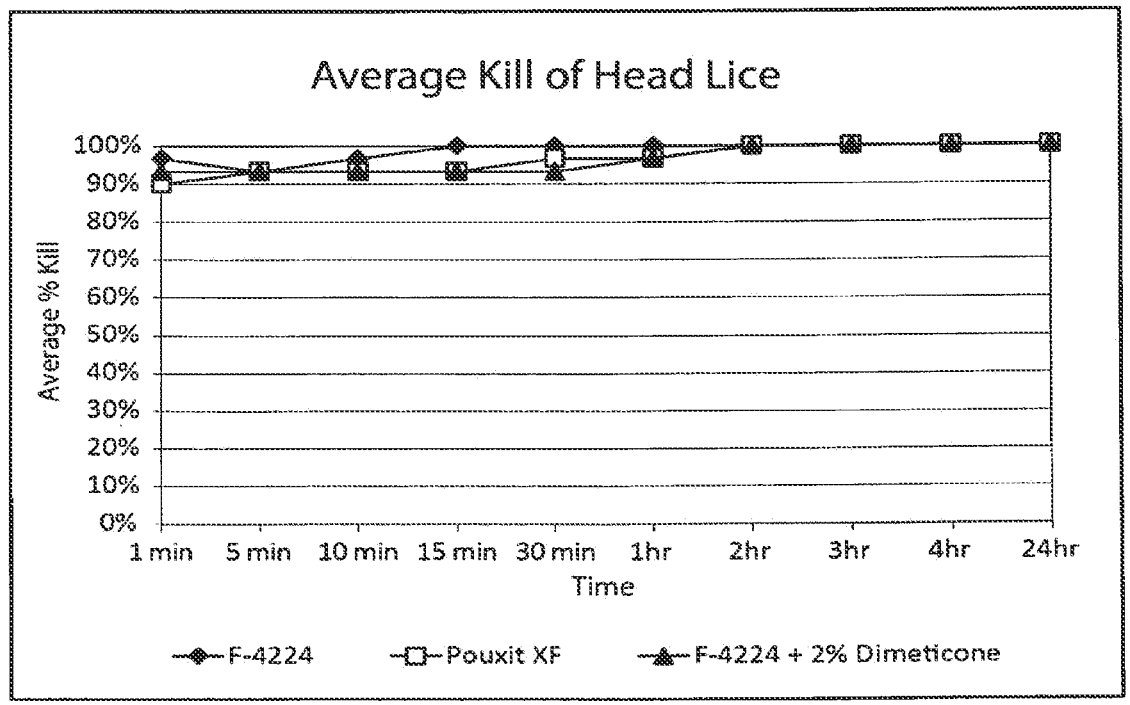
FIG. 12 shows the mortality efficacy of a 15 minute exposure of various compositions against head lice. In vitro dip method.
Figure 13:
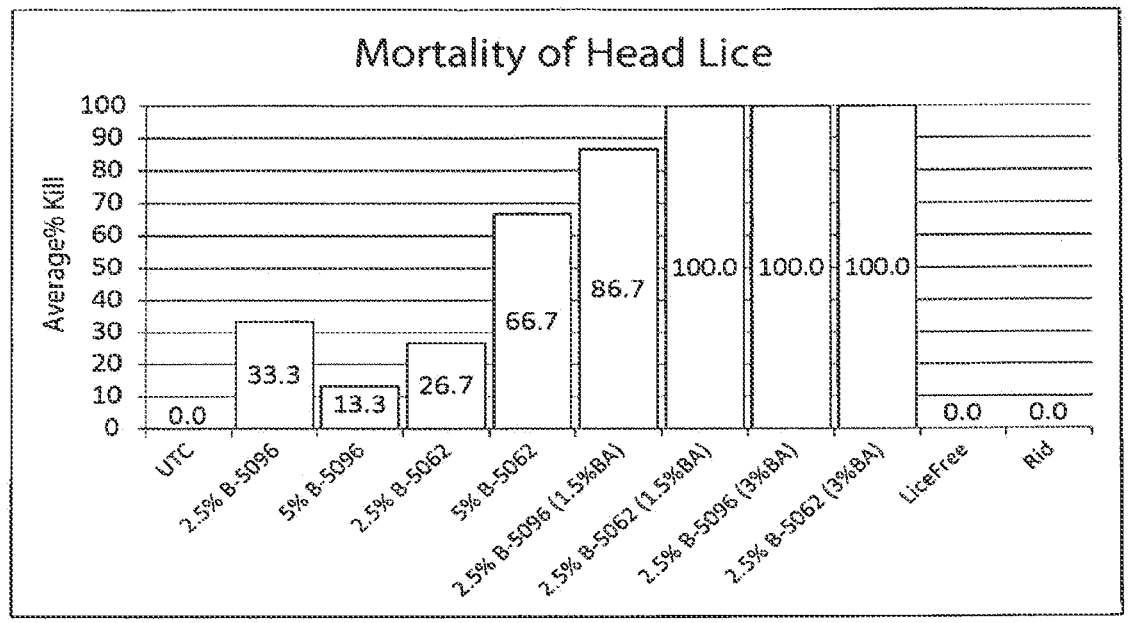
FIG. 13 shows the mortality efficacy of various compositions against head lice. BA=benzyl alcohol. n=10.
Figure 15:
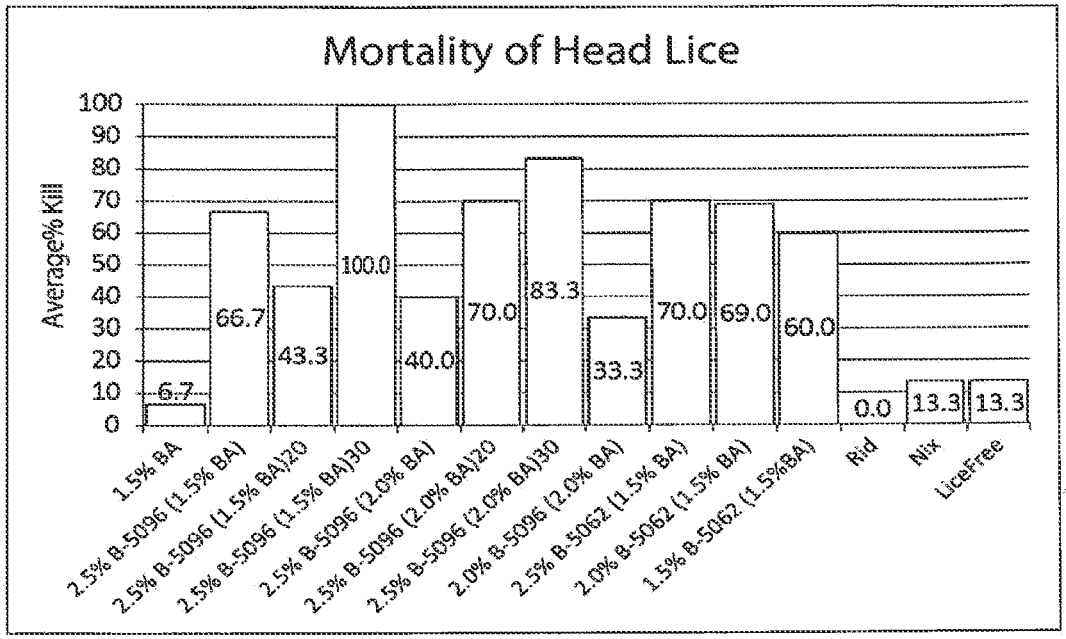
FIG. 15 shows the mortality efficacy of a 10 minute exposure various compositions against head lice. n=30.

| Name | Ingredients | Reference |
|---|---|---|
| Base | Isopropyl alcohol, butyl lactate, Stepanol WAC and DI Water | FIG. 1 |
| TT HL Killer *TT-5096 *TT 5096 F-4224 Clinical B-5096 treatment | geraniol, vanillin, IPM, TEC, Benzyl alcohol, Isopropyl alcohol, Butyl Lactate, Stepanol WAC, Germaben II, A-46 Propellent, DI Water | FIG. 1, 2, 3, 6, 9, 10, 11, 12 |
| Control Water control Water | 100% DI Water | FIG. 2, 3, 4 |
| TyraTech 0831 TTN-0831 B-5062 | Geraniol, thyme oil white 3, linalool, THL, vanillin, IPM, heliotropine, TEC—in Equate baby shampoo as base | FIG. 4, 8 |
| TT-HLK + 2.5% Eucalyptus | Eucalyptus, geraniol, vanillin, IPM, TEC, Benzyl alcohol, Isopropyl alcohol, Butyl Lactate, Stepanol WAC, Germaben II, A-46 Propellent, DI Water | FIG. 3 |
| TyraTech | Geraniol, thyme oil white 3, linalool, THL, vanillin, IPM, heliotropine, TEC Benzyl alcohol, Isopropyl alcohol, Butyl Lactate, Stepanol WAC, DI Water | FIG. 5 |
| F-4224 + 2% Dimeticone | dimeticone, geraniol, vanillin, IPM, TEC, Benzyl alcohol, Isopropyl alcohol, Butyl Lactate, Stepanol WAC, Germaben II, A-46 Propellent, DI Water | FIG. 9, 10, 11, 12 |
| B-5096 | Geraniol, vanillin, IPM, TEC—Isopropyl alcohol, butyl lactate, Stepanol WAC and DI Water | FIG. 13, 14 |
| B-5062 | Geraniol, thyme oil white 3, linalool, THL, vanillin, IPM, heliotropine, TEC—Isopropyl alcohol, butyl lactate, Stepanol WAC and DI Water | FIG. 13, 14 |
| B-5096 | Geraniol, vanillin, IPM, TEC—Isopropyl alcohol, butyl lactate, Stepanol WAC, Germaben II, A-46 Propellent and DI Water | FIG. 15, 16 |
| B-5062 | Geraniol, thyme oil white 3, linalool, THL, vanillin, IPM, heliotropine, TEC—Isopropyl alcohol, butyl lactate, Stepanol WAC, Germaben II, A-46 Propellent and DI Water | FIG. 15, 16 |
| BA | Benzyl alcohol | FIG. 13, 14, 15, 16 |
| NIX ® | Commercial formula—NIX ® Lice Treatment Créme Rinse: 1% permethrin | FIG. 2 |
| RID ® | Commercial formula—RID ®Lice Killing Shampoo: 0.33% pyrethrins/4% PBO | FIG. 2 |
| LICESHIELD | Commercial formula | FIG. 3 |
| Pouxit XF | Commercial formula—Pouxit XF: dimeticone | FIG. 9 |
| LICEFREEE! ™ | Commercial formula | FIG. 13, 14 |

TABLE 3-continued

Ingredients of Compositions used in Examples.

| Name | Ingredients | Reference |
| --- | --- | --- |
| TT Personal Repellent | geraniol, vanillin, lauric acid, IPM, TEC, Isopropanol, White mineral oil, vitimine E | FIG. 3 |

Example 1

Mode of Action Study

Assay was designed to test the mortality of products against all stages of head lice using a standard dip method protocol, as described in this Example 1. Head lice were collected from patients and put into moist filter paper lined petri dishes. 10 head lice per replication were treated, rinsed, and evaluated. The procedure was repeated 3 times and evaluated at 1.0, 2.0, 3.0, and 4.0 hours. Time of death was recorded when all movement and peristalsis of the gut ceases.

Target species: *Pediculus humanus* capitis (Head Louse). Test Species per replication: 10 lice. Dip bioassay (6 ml of solution) with 15 minute exposure to treatment. Mortality was assessed at one, two, three, and four hours post-treatment. Treatments were performed during the daytime, between 10 am and 4 pm. Death was the evaluation parameter. Minimum number of replicates: 20.

The collecting technicians washed their hands with anti-bacterial soap and rinse in clean tap water, followed by a rinse of 70% alcohol to remove any possible contaminants. Using a lighted circular 15× magnifying lamp, the technicians removed the lice from heads of infested individuals with entomological forceps to avoid physical damage to the lice. These lice were placed in a glass Petri dish (100×15 mm) each containing a 100% cotton circular cloth disk which had been dampened with filtered or distilled water to prevent the lice from dehydration. Specimens were examined with a microscope by the investigator for viability, intact legs and antennae.

New cotton cloths were washed with a small quantity of non-medicated anionic shampoo (Pre11). Towels were thoroughly rinsed and machine dried. Twenty centimeter diameter disks were cut from these prepared towels. This specific cloth was used for the simulation of hair. Multiple subjects were used as the source for all the lice used in this study. Lice of different stages of both genders were gently transferred from infested participants to the test dishes using entomological forceps to avoid physical damage to the lice. Lice removed from the subjects' hair were stored in an incubator and used within two hours of collection. The incubator temperature were maintained at 31.7(±0.50) C (890F) and at a relative humidity of 60±10%.

At the start of the test, 10 lice were put into the bottom of a 60×15 mm petri and 6 ml of the test formula were measured into a sterile glass vial and dumped onto the lice and allowed to sit for a specified time i.e., 15 minutes. A glass stir rod was carefully used to gently mix the material around to remove air bubbles. A cloth disk was then put on top of the material to keep any lice from floating to the surface of the treatment. After a set time the lice were dumped onto a sieve and washed with tepid water until all treatment was removed. Using soft touch forceps the lice were transferred onto a moist filter paper covered petri dish (100×15 mm) and observed for 4 hours and again at 24 hours post treatment. Time of death was recorded when all movement and peristalsis of the gut ceases. Tests were conducted under artificial lighting at laboratory temperatures of 72°.

Louse must fit specific qualifications prior to test. Must not act or look to be damaged or injured; must have all six legs. Louse had not been treated while on the patient at anytime. Louse was used within 4 hour after the louse was collected off patient; while awaiting testing, louse was put into an environmental chamber with a temperature between 31.7±2 degrees Celsius with relative humidity between 30-60 percent.

The objective of this experiment was to examine Geraniol, IPM, Benzyl Alcohol, butyl lactate, vanillin, and triethyl citrate independently and in combination to provide information about the contribution of each component to further elucidate the mode of action of each component. It has been well-established (Lei, et al. (2010). Nematicidal activity of two monoterpenoids and SER-2 tyramine receptor of *Caenorhabditis elegans*. Biochemical Pharmacology, 79(7), 1062-1071) that the mode of action of geraniol and other essential oils is neurological, via neuroreceptors. Benzyl alcohol and Isopropyl myristate may act via neuroreceptors; additionally, and/or alternatively, each may act via physical means (i.e., as a desiccant, a smothering agent, and/or a "stripping" agent that removes lipids from an insect's cuticle). Geraniol alone provided 10% mortality at four hours. Isopropyl myristate alone provided 0% mortality at four hours. Benzyl alcohol alone provided 3% mortality at four hours. A combination of isopropyl myristate and benzyl alcohol provided 70% mortality. A combination of isopropyl myristate and geraniol provided 57% mortality. A combination of geraniol and benzyl alcohol provided 53% mortality. TT HL Killer provided 100% mortality at four hours post-treatment. See FIG. 1.

Example 2

Average Percent Mortality at 4 Hours Post-Treatment

Three treatment groups plus a water control: (1) TyraTech mousse: 2.5% (TT5096); (2) RID® Lice Killing Shampoo: 0.33% pyrethrins/4% PBO; (3) NIX® Lice Treatment Crème Rinse: 1 permethrin. Standard dip method protocol, as described in Example 1, with ten minute or 30 minute exposure, after which there was a water rinse. Ten lice/replicate (5 adults, 5 immatures). Three replicates per treatment. Final KD and mortality evaluated at 4 hours post-treatment. Pyrethroid/permethrin-resistant head lice collected from human subjects and tested within 30 minutes. TyraTech's mousse formulation provided 100% mortality of insecticide resistant head lice when exposed for 30 minutes vs. 0% for the market leaders RID® and 13% for NIX®. See FIG. 2.

Example 3

Head Lice Repellency Using Treated Human Hair Tuffs

Human hair bundle bioassay. Assay was designed to test the repellency of products against all stages of human head lice. Human head lice are collected from patients and and randomly placed into filter paper lined petri dishes. Tuffs of hair 3-4 mm thick are treated and held in front of a running louse. The procedure is replicated 20 times at a designated time period. It was noted whether the louse grab onto the hair and measure how far it traveled up the tuff.

Target species: *Pediculus humanus capitis* (Head Louse). Twenty Test Species per replication. Dip method used with 30 second exposure time. Treatment time was during the day, between 10 am and 3 pm. Evaluation parameters: Percent failure to attach and percent repellency. Minimum number of replicates: 20. Evaluation time points: 1 hour.

The collecting technicians washed their hands with antibacterial soap and rinsed in clean tap water, followed by a rinse in 70% alcohol to remove any possible contaminants. Using a lighted circular 15× magnifying lamp, the technicians removed the lice from heads of infested individuals with entomological forceps to avoid physical damage to the lice. These lice were placed in a glass Petri dish (5.5 cm) each containing a 100% cotton circular cloth disk which was dampened with filtered or distilled water to prevent the lice from dehydration. Specimens were examined with a 15× hand lens by the investigator for viability, intact legs and antennae.

Human hair was collected and rolled into several 3-4 mm thick tuffs and cut to 5 cm long. To insure the tuffs did not fall apart, the tips of the hair tuffs were dipped into a heated and melted carnauba wax mixture. Once all lice were collected, the tuffs of hair were dipped into bottles containing four substances and left to soak for 2 minutes. They were then stuck onto lab tape and left to hang. One hour after treatment testing was initiated. Lice were placed in the center of the petri dish. An untreated hair bundle is presented to the lice for 30 seconds. Lice which did not attach to the hair or migrate vertically up the hair bundle more than 5 mm were excluded from the test and a new louse was selected. A treated hair tuft was then presented to the qualified louse for a duration of 30 seconds and response was measured. It was noted whether the louse stopped in front of the hair (failed to attach) and/or grabbed ahold of the hair. Once the louse attached to the hair bundle the vertical distance traveled was measured using a ruler. If the louse attached to the bundle and traveled farther than 5 mm it is categorized as non-repelled.

Louse must fit specific qualifications prior to test. Must not act or look to be damaged or injured; must have all six legs. Louse had not been treated while on the patient at anytime. Louse was used within 4 hour after the louse was collected off patient; while-awaiting testing, louse was put into an environmental chamber with a temperature between 31.7±2 degrees Celsius with relative humidity between 30-60 percent.

Four compositions were compared for repellent effect against louse. Control sample was water. TT Personal repellent: 10% of lice failed to attach to hair bundle within 30 secs; 40% considered repelled (i.e., did not travel farther than 5 mm). TT Head Lice killer: 50% of the lice failed to attach; 90% repelled. LICESHIELD: 5% failed to attach; 75% repelled. TT Head Lice killer combined with 2.5% *eucalyptus* demonstrated 100% repellency. See FIG. 3.

Example 4

Efficacy of TTN-0831 in Shampoo Base Versus Nix

Dip test, as described in Example 1, comparing TTN-0831 (5% active) in shampoo base at both 20 minute and 30 minute exposures, commercially-available NIX® (1% permethrin active) at 10 minute exposure (per label instructions), and water control. Mortality was evaluated at four hours post-treatment. The data (see Table 4) show that TTN-0831 at both 20 and 30 minute exposure times was approximately 3 times more effective in controlling head lice than NIX® (permethrin) shampoo. See FIG. 4. A commercially available shampoo was used for this example but the shampoo base is considered to be generally interchangeable with other shampoos and the particular shampoo is not considered to be an essential component in the formulation.

TABLE 4

Percent mortality of lice 4 hours post-treatment.

|  | Head Lice Percentage Dead |
|---|---|
| TTN-0831 20 Minute Dip (N = 26) | 85% |
| TTN-0831 30 Minute Dip (N = 34) | 88% |
| NIX ® 10 Minute Dip (N = 20) | 30% |
| Water Control (N = 30) | 0% |

Example 5

In Vitro Efficacy Study: Speed of Action

Dip test, as described in Example 1, comparing knockdown (KD) measured in three treatment groups: TyraTech formulation, RID®, and NIX®. Knockdown is determined when lice are inactive, no movement even when probed. Head Lice knockdown and mortality appears to occur rapidly (at 5 minutes post-treatment) with the TyraTech formulation—none of the lice recover, even at three hours post-treatment. RID® demonstrated some early knockdown but by 3 hours, 100% of the treated lice were active indicating partial recovery and no mortality. 100% of the NIX® treated lice were fully or partially active at all post-treatment intervals with no mortality observed (i.e., inactive). These tests were performed on pyrethroid-resistant populations of lice. Formula optimization with benzyl alcohol and dose response of each treatment group over time. See FIG. 5.

Example 6

In-Vivo Clinical Study

Randomized, open label clinical in-vivo study to compare average head lice control of TyraTech mousse formulations TT-5096 and TT-5062 against commercially available NIX® creme rinse. The primary objective of the study was to compare the efficacy and safety of TyraTech mousse TT-5096 formula against NIX® on subject with head lice immediately following the initial application, 7 days following the initial application (Day 8), and 14 days following the initial application (Day 15).

Inclusion criteria: male or female over the age of 4 with active head lice infestation of live lice at the screening visit and a presence of nits who agree to not use any lice comb or any other pediculicides or medicated hair grooming products for the duration of the study. Exclusion criteria: subjects had not used any other form of head lice treatment whether prescription or over-the-counter (OTC) or home remedy for at least four (4) weeks prior to their Screening visit (Day 1); subjects had not used any topical medication of any kind on the hair for a period of 48 hours prior to the Screening visit; a history of allergy or hypersensitivity to ragweed or any ingredient in either test product; subjects with any visible skin/scalp condition at the treatment site which, in the opinion of the investigative personnel, will interfere with the evaluation of the test product; Females who are pregnant or nursing.

Subjects had the test product applied on Day 1 by investigative site personnel after it has been determined they are eligible for the study. The date and start time of the application of the test product was recorded as well as the time the hair is considered dry or start time of the rinse. The amount, by weight, of test product applied was recorded. Subjects were asked to abstain from taking prescription or non-prescription medications for the treatment of lice other than the test product beginning 4 weeks prior to the Screening visit through the end of the study. Subjects were also asked to abstain using any home remedies for the treatment of lice other than the test product beginning 4 weeks prior to the Screening visit through the end of the study. An assessment of the hair and scalp was performed to determine the number of live lice observed at pre-treatment on Day 1 and Day 8, immediately post-treatment on Day 1 and on Day 8, and on Days 15. An estimate of the number of nits present was made prior to treatment only. Each assessment noted the total number of live lice observed based on those observed in the left, middle, and right side of the head. Demographic information is included in Table 5.

TABLE 5

Demographic information of test subjects.
Demographic Characteristics

|  | TT-5096 n 33 | TT-5096 % | NIX® n 31 | NIX® % |
|---|---|---|---|---|
| Gender |  |  |  |  |
| Male | 5 | 15.15 | 2 | 6.45 |
| Female | 27 | 81.82 | 29 | 93.55 |
| Age |  |  |  |  |
| mean | 13.8 |  | 14.8 |  |
| range | 5, 42 |  | 4, 50 |  |
| Race |  |  |  |  |
| White | 31 | 93.94 | 27 | 87.10 |
| Black | 1 | 3.03 | 4 | 12.90 |
| Ethnicity |  |  |  |  |
| Hispanic | 23 | 69.70 | 23 | 74.19 |
| Non-Hispanic | 10 | 30.30 | 8 | 25.81 |
| Hair Length |  |  |  |  |
| Short | 3 | 9.09 | 2 | 6.45 |
| Medium | 12 | 36.36 | 9 | 29.03 |
| Long | 15 | 45.45 | 17 | 54.84 |
| Very Long | 3 | 9.09 | 3 | 9.68 |
| Hair Curliness |  |  |  |  |
| Straight | 14 | 42.42 | 12 | 38.71 |
| Wavy | 17 | 51.52 | 17 | 54.84 |
| Curly | 2 | 6.06 | 2 | 6.45 |
| Hair Texture |  |  |  |  |
| Fine | 1 | 3.03 | 8 | 25.81 |
| Average | 28 | 84.85 | 21 | 67.74 |
| Coarse | 4 | 12.12 | 2 | 6.45 |

For the TyraTech mousse formulation TT-5096 treatment, test subject's hair was saturated with TyraTech mousse formulation TT-5096 and kept on for 30 minutes; hair was rinsed with warm water and then shampooed with Johnson Baby Shampoo. No nit combs were used to test solely the activity of the mousse formulation. For the NIX® Crème rinse treatment, test subject's hair was saturated with NIX® and kept on for 10 minutes, per label instructions; hair was rinsed with warm water and then toweled dry. Again, no nit combs were used. A sample size of 33 subjects in one group (TyraTech's head lice mousse) and 31 in the other group (NIX®) is a feasible sample size to provide descriptive statistics for the efficacy and safety parameters. Secondary characteristics of the lice infestation (erythema, pruritus, infection, excoriation, and dry scalp) are comparable across both treatment groups with exception of dry scalp where more TT-5096 subjects had a greater improvement than those receiving NIX® (change from Baseline at Day 8 and 15).

Figure 6:
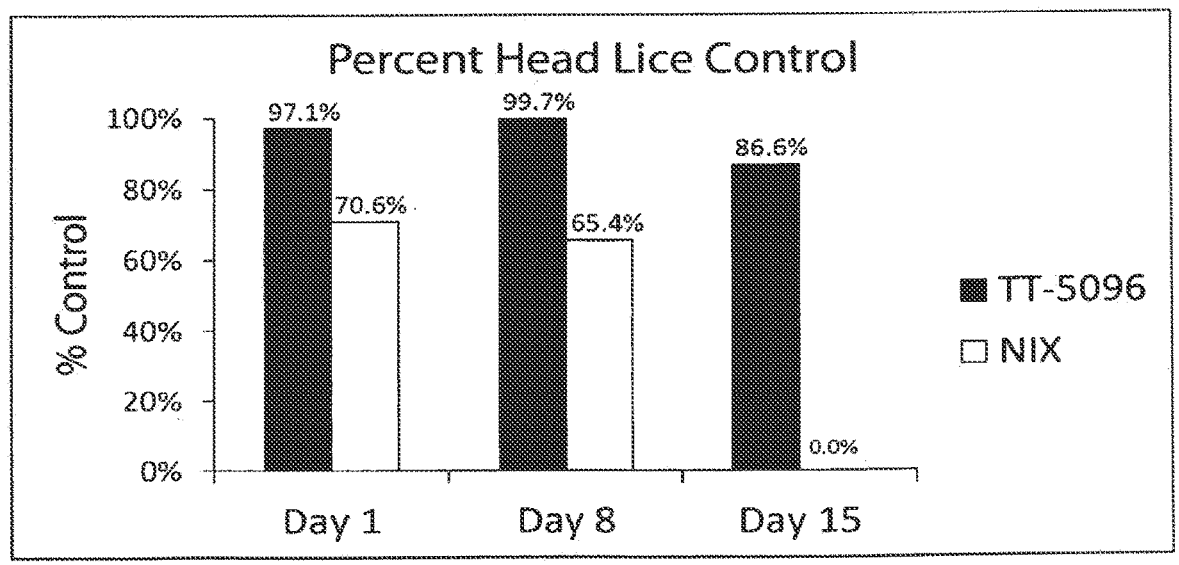
FIG. 6 shows results from an in vivo clinical study testing the percent reduction of head lice after treatment with TyraTech formulation TT-5096 or NIX®.

Two treatment applications at day 1 and day 8. Results of the clinical study (64 patients) demonstrated that TyraTech's head lice mousse (N=33) provided significantly higher reductions in head lice at day 1 (97%) and day 8 (99%) vs. NIX® (N=31) at day 1 (71%) and day 8 (65%). Percent reductions of each treatment were based on pretreatment lice counts. The overall reduction at two weeks for the TyraTech mousse treatment dropped slightly to 82% (N=33) likely due to head lice re-infestation from untreated siblings. By two weeks (day 15), the NIX® treatment had totally failed (0% with N=31); all test subjects had lice. This was largely due to well documented insecticide resistance (permethrin) in the head lice population and lack of nit control. See FIG. 6.

Figure 7:
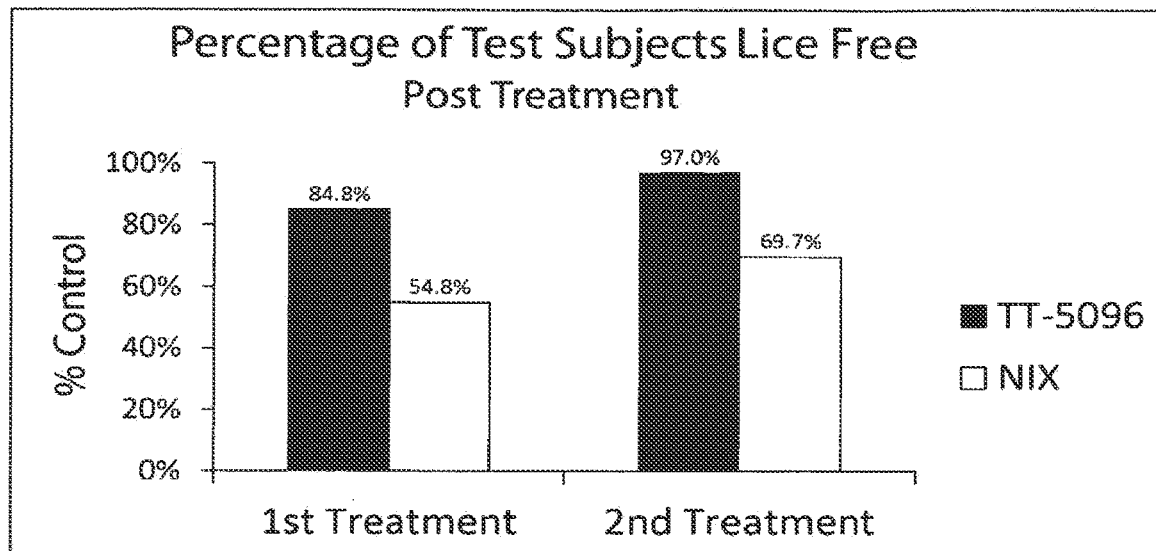
FIG. 7 shows the percentage of test subjects that were lice free after treatment with the TyraTech formulation TT-5096 or NIX®.

FIG. 7 shows the percentage of test subjects lice free after reduction in head lice at one week (n=33) vs. 47% reduction with the NIX® treatment (n=31). The first treatment was performed at day 1; the second treatment was performed at day 8. The data show that 85% of test subjects treated with the TyraTech formulation (TT-5096) were lice free after the first treatment, versus 55% of test subjects treated with NIX®. The data show that 97% of test subjects treated with the TyraTech formulation (TT-5096) were lice free after the second treatment, versus 70% of test subjects treated with NIX®. Following the initial treatment (Baseline), the percentage of subjects with no lice observed in the TT-5096 group was significantly higher than in the NIX® group (84.85% (28/33), TT-5096; 54.84% (17/31), NIX®); however, one week later (Day 8) prior to treatment, those with no lice observed was similar across treatment groups (45.45% (15/33), TT-5096; 45.16% (14/31), NIX®). Following repeat treatment on Day 8, TT-5096 was significantly more effective than NIX® when looking at the number of subjects with no lice observed (96.97% (32/33), TT-5096, 74.19% (23/31), NIX®). One week later at the Day 15 visit, the percentage of subjects with no lice observed diminished from that post-treatment on Day 8 but was significantly greater in the TT-5096 group (51.52% (17/33), TT-5096, 25.81% (8/31), NIX®) than in the NIX® group. The Killing Rate is significantly greater following use of TT-5096 (82.1%) compared to NIX® (10.2%). Table 6 contains raw data.

TABLE 6

Raw data of Efficacy Results of FIG. 7.

|  | TT-5096 n 33 | TT-5096 % | NIX® n 31 | NIX® % |
|---|---|---|---|---|
| Day 1 Pre-treatment—mean | 20.97 |  | 11.29 |  |
| Day 1 Pre-treatment—range | 4, 107 |  | 4, 38 |  |
| Day 1 Pre-treatment—standard deviation | 24.39 |  | 10.10 |  |

TABLE 6-continued

Raw data of Efficacy Results of FIG. 7.

|  | TT-5096 n 33 | TT-5096 % | NIX® n 31 | NIX® % |
|---|---|---|---|---|
| Day 1 Post-treatment—mean | 0.61 | | 3.32 | |
| Day 1 Post-treatment—standard deviation | 1.54 | | 8.22 | |
| Day 1 Post-treatment—95% confidence interval | 0.53 | | 2.89 | |
| Day 1 Post-treatment—range | 0, 6 | | 0, 37 | |
| Day 1—Number with NO lice Post-Treatment | 28 | 84.85 | 17 | 54.84 |
| Day 1 Nits—mean | 411.45 | | 253.19 | |
| Day 1 Nits—range | 38, 1100 | | 8, 1010 | |
| Day 8 Pre-treatment—mean | 3.39 | | 4.77 | |
| Day 8 Pre-treatment—standard deviation | 7.73 | | 9.76 | |
| Day 8 Pre-treatment—95% confidence interval | 2.64 | | 3.43 | |
| Day 8 Pre-treatment—range | 0, 43 | | 4, 42 | |
| Day 8 Pre-treatment—NO lice | 15 | 45.45 | 14 | 45.16 |
| Day 8 Post-treatment—mean | 0.09 | | 1.65 | |
| Day 8 Post-treatment—standard deviation | 0.51 | | 4.10 | |
| Day 8 Post-treatment—95% confidence interval | 0.18 | | 1.44 | |
| Day 8 Post-treatment—range | 0, 3 | | 0, 20 | |
| Day 8 Post-treatment—NO lice | 32 | 96.97 | 23 | 74.19 |
| Day 15—mean | 2.82 | | 11.58 | |
| Day 15—range | 0, 22 | | 0, 93 | |
| Day 15—NO lice | 17 | 51.52 | 8 | 25.81 |
| Day 15—standard deviation | 4.72 | | 20.29 | |
| Day 15—95% confidence interval | 1.61 | | 7.14 | |

Example 7

In Vitro Study: 1 Hour Knockdown and 24 Hour Mortality

Three TyraTech formulations: TyraTech 2.5% B-5096 (2.5% B-5096), TyraTech 5% B-5096 (5% B-5096), and TyraTech 2.5% B-5062 (2.5% B-5062) were tested for 1 hr knockdown and 24-hour mortality against adult body lice, *Pediculus humanus humanus*, using ASTM protocol E938-94, as follows:

Place 25 adult lice, mixed sexes, in the bottom of the 9-dram test container. Insert the screened plunger to keep the lice from floating to the surface. Place the pediculicide to be tested in a 100-ml beaker and introduce the beaker into a water bath maintained at 32° C. Allow the test formulation temperature to stabilize prior to testing. Place the 9-dram vial in the 100-ml pediculicide beaker, and keep the lice under the pediculicide for 10 min. Remove the test container and blot the bottom of the container to remove any remaining liquid. Place the 9-dram vial into the 1000-ml beaker containing distilled water at 32° C. and agitate the container. At the end of 1 min, remove container, and gently wash lice in a stream of distilled water (32° C.) from the wash bottle for 1 min. Blot excess water with paper toweling. Transfer the lice to a clean 4 by 4-cm patch of dark corduroy cloth. Use a camel hair brush to remove any lice that remain in the container. Place corduroy patch in a petri dish. Place the petri dish with lice in an incubator maintained at 31.7° C. and 60% RH. Make the first observation 1 h post treatment, and replace the petri dish in the incubator. To make an observation, place the lice on top of a patch in a petri dish, which is then placed on the slide warmer (31.7° C.). Lice not dead or morbid will move to the lower patch within 5 min. For the controls, repeat all of the above procedures, substituting distilled water for the candidate pediculicide.

The average corrected knockdown and mortality are shown in Table 7:

TABLE 7

Percentage knockdown and mortality.

| Formulation | 1-Hour KD (%) | 24-Hour Mortality (%) |
|---|---|---|
| Control | 0 | 8.0 |
| 2.5% B-5096 | 49.6 | 20.9 |
| 5% B-5096 | 60.0 | 18.3 |
| 2.5% B-5062 | 82.4 | 63.5 |

The 2.5% B-5096 and 5% B-5096 formulations provided 49.6% and 60% knockdown at 1 hour respectively. The 2.5% B-5062 formulation provided 82.4% knockdown at 1 hour. The 2.5% B-5096 and 5% B-5096 formulations provided 20.9% and 18.3% mortality respectively after Abbott's formulation correction for control mortality. The 2.5% B-5062 provided 63.5% mortality at 24 hours. There was no control knockdown at 1 hour but there was 8.0% control mortality at 24 hours.

Example 8

In Vitro Study: 1 Hour Knockdown and 24 Hour Mortality

Four TyraTech formulations: TyraTech 3% B-5062 (3% B-5062), TyraTech 5% B-5062 (5% B-5062), TyraTech 7% B-5062 (7% B-5062), and TyraTech 10% B-5062 (10% B-5062) were tested for 1 hr knockdown and 24-hour mortality against adult body lice, *Pediculus humanus*, using ASTM protocol E938-94, as described in Example 8. The average corrected knockdown and mortality are shown in Table 8.

TABLE 8

Percentage knockdown and mortality.

| Formulation | 1-Hour KD (%) | 24-Hour Mortality (%) |
|---|---|---|
| Control | 4.0 | 7.2 |
| 3% B-5062 | 57.5 | 43.1 |
| 5% B-5062 | 57.5 | 51.7 |
| 7% B-5062 | 58.3 | 37.9 |
| 10% B-5062 | 66.7 | 33.6 |

Figure 8:
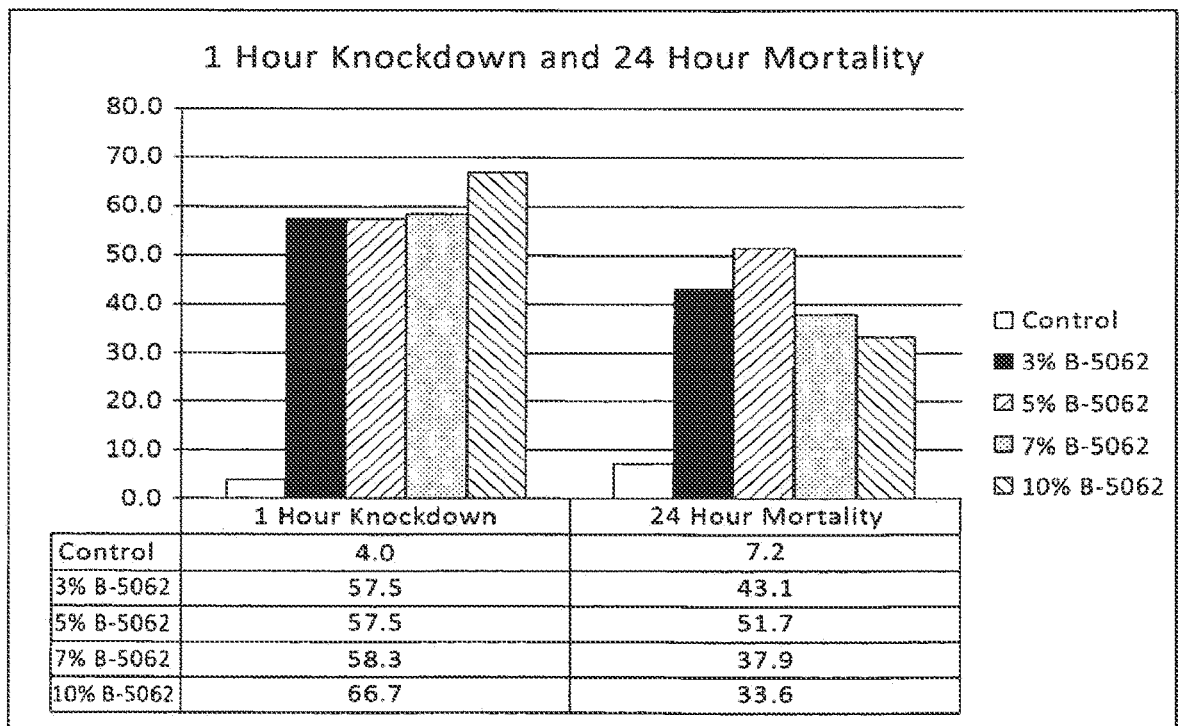
FIG. 8 shows the knockdown effects of various compositions against adult body lice 1 hour after treatment and the percent mortality of the lice 24 hours after treatment with these compositions.

None of the four formulations provided greater than 70% knockdown at 1 hour. The 3% B-5062 and 5% B-5062 both caused 57.5% knockdown, the 7% B-5062 caused 58.3% knockdown and the 10% B-5062 provided 66.7% knockdown at 1 hour. The only formulation to cause greater than 50% mortality at 24 hours was the 5% B-5062. The 3% B-5062 caused 43.1% mortality, the 5% B-5062 caused 51.7% mortality, 7% B-5062 caused 37.9% mortality and the 10% B-5062 caused 33.6% mortality by 24 hours. There was 4.0% knockdown in the control at 1 hour and 7.2% mortality by 24 hours. See FIG. 8.

Example 9

Comparison Against Dimeticone Product

Standard dip method protocol, as described in Example 1, comparing both knockdown and kill of three compositions:

(1) TyraTech F-4224; (2) Pouxit XF; and (3) TyraTech F-4224+2% dimeticone. Pouxit XF is commercially available, with 4% dimeticone as its active ingredient. All samples were assessed at 5, 10, and 15 min exposures. Exposure times did not significantly change efficacy for any of the treatments. TyraTech F-4224 and TyraTech F-4224+2% dimeticone are about 1½-2 hours faster to knockdown and kill versus Pouxit XF treatments. See FIGS. 9-12.

Example 10

Effect of the Addition of Benzyl Alcohol on Mortality

Standard dip method protocol, as described in Example 1. Efficacy (mortality) of the following compositions was measured four hours post-treatment: (1) TyraTech composition 2.5% B-5096; (2) 5% B-5096; (3) 2.5% B-5062; (4) 5% B-5062; (5) 2.5% B-5096+1.5% benzyl alcohol; (6) 2.5% B-5062+1.5% benzyl alcohol; (7) 2.5% B-5096+3% benzyl alcohol; (8) 2.5% B-5062+3% benzyl alcohol; (9) LICEFREEE!™; (10) RID®; and (11) untreated water control. Both RID® and LICEFREEE!™ are commercially available products. The addition of benzyl alcohol improved the performance of both TyraTech experimental compositions. Both RID® and LICEFREEE!™ displayed 0% mortality at four hours. See FIG. 13.

Example 11

Effect of the Addition of Benzyl Alcohol on Knockdown

Figure 14:
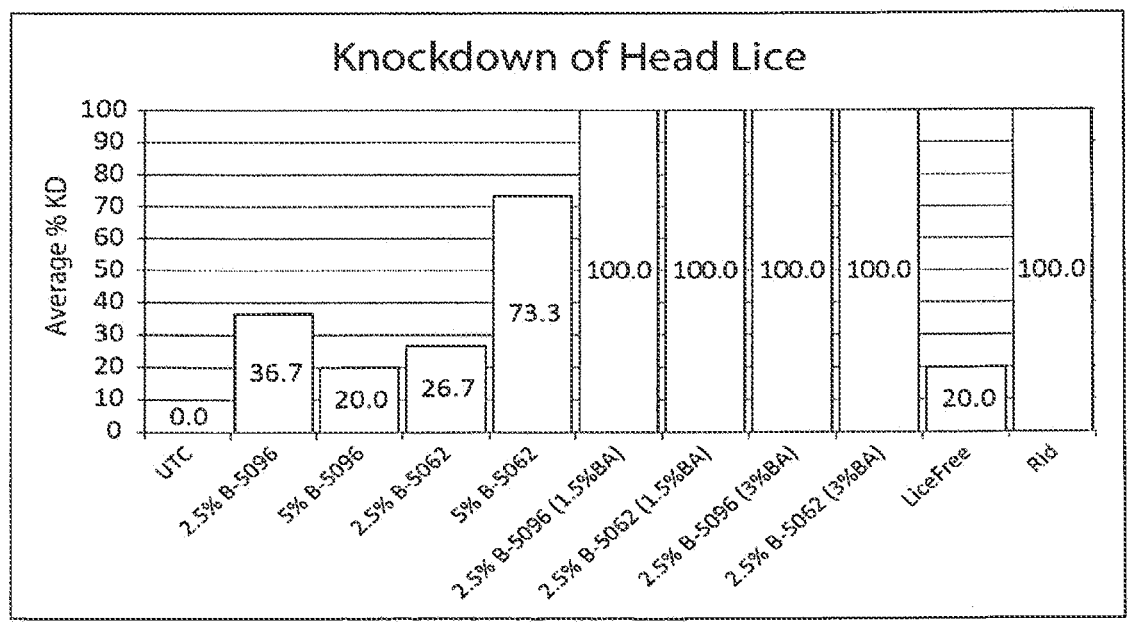
FIG. 14 shows the knockdown efficacy of various compositions against head lice. BA=benzyl alcohol. Knockdown=partially active+inactive, n=10

Standard dip method protocol, as described in Example 1. Efficacy (knockdown) of the following compositions was measured four hours post-treatment: (1) TyraTech composition 2.5% B-5096; (2) 5% B-5096; (3) 2.5% B-5062; (4) 5% B-5062; (5) 2.5% B-5096-+1.5% benzyl alcohol; (6) 2.5% B-5062+1.5% benzyl alcohol; (7) 2.5% B-5096+3% benzyl alcohol; (8) 2.5% B-5062+3% benzyl alcohol; (9) LICEFREEE!™; (10) RID®; and (11) untreated water control. Both RID® and LICEFREEE!™ are commercially available products. The addition of benzyl alcohol improved the performance of both TyraTech experimental compositions. RID® provided 100% knockdown at four hours, while LICEFREEE!™ provided 20%. See FIG. 14.

Example 12

Figure 16:
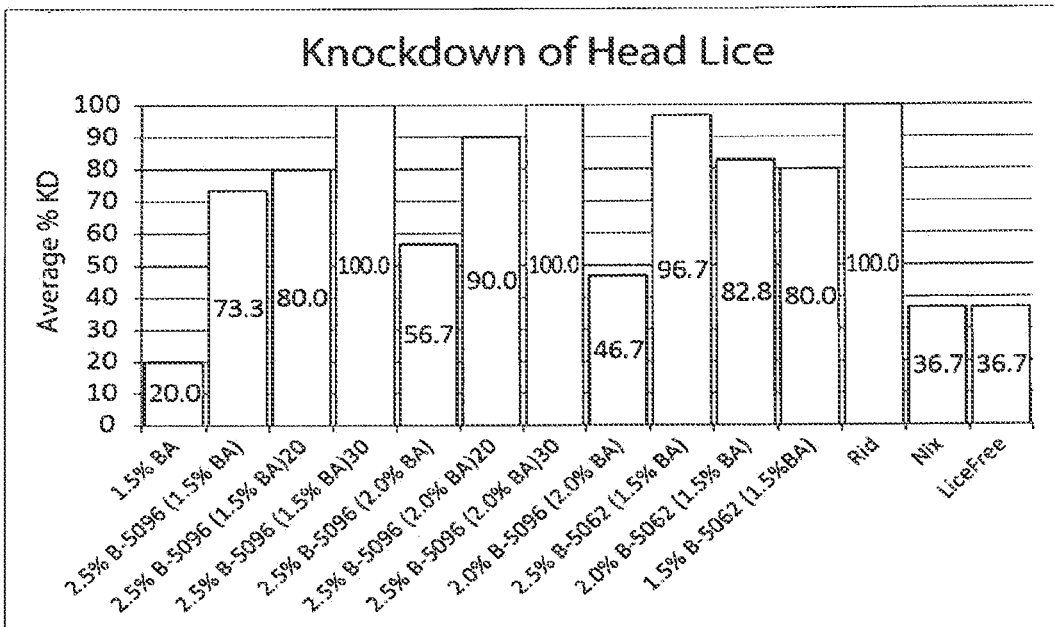
FIG. 16 shows the knockdowns effects after a 10 minute exposure of various compositions against head lice. Knockdown=partially active+inactive, n=30.

Standard dip method protocol, as described in Example 1. Dose response study evaluating: exposure time (i.e., 10 min, 20 min, 30 min); composition (i.e., B-5096, B-5062); concentration of composition (i.e., 1.5%, 2.0%, 2.5%); addition of benzyl alcohol; and concentration of benzyl alcohol. Three commercially available products (RID®, NIX®, and LICEFREEE!™) were also evaluated. RID® provided 100% KD, 0% kill; NIX® and LICEFREEE!™ about 36% KD, 13% kill. Take home: dose response by time and by concentration of specifically: Same increase activity as increase concentration of blend. Increase in activity in increase of time exposed. See FIGS. 15 and 16.

TABLE 9

TyraTech test samples.

| Ingredients | TT-A | TT-B | TT-C | TT-D | TT-E | TT-F | TT-Control |
|---|---|---|---|---|---|---|---|
| B-5096 | 2.5 | 2.5 | 2 | | | | 0 |
| B-5062 | | | | 2.5 | 2 | 1.5 | 0 |
| Benzyl Alcohol | 1.50 | 2.00 | 2.00 | 1.50 | 1.50 | 1.50 | 1.50 |
| IPA, anhyd. | 1.50 | 1.50 | 1.50 | 1.50 | 1.50 | 1.50 | 1.50 |
| Butyl Lactate | 1.25 | 1.25 | 1.25 | 1.25 | 1.25 | 1.25 | 1.25 |
| Stepanol WAC, extra | 0.45 | 0.45 | 0.45 | 0.45 | 0.45 | 0.45 | 0.45 |
| Water | 86.6 | 86.1 | 86.6 | 86.6 | 87.1 | 87.6 | 89.1 |
| Germaben II | 0.20 | 0.25 | 0.25 | 0.25 | 0.25 | 0.25 | 0.25 |
| A-46 | 6.00 | 6.00 | 6.00 | 6.00 | 6.00 | 6.00 | 6.00 |

Example 13

Efficacy of TT-4301 Against Lice Nits

This test method determines the effectiveness of ovicidal materials in liquid, gel, cream, or shampoo form against the ova (that is, eggs or nits) of the human louse, *Pediculus humanus*. Five replicates of 30 eggs are immersed in a test compound for a set period of time, washed, rinsed, blotted, dried, and incubated. Five control replicates are attached to human hair and processed as the treatment replicates, but with immersion in water. Percent egg mortality, corrected by Abbott's Formula, is determined.

Egg-infested hairs are attached to the end of a wooden applicator stick with duct tape such that 30 nits are on 1 to 3 hairs. Each replicate of 30 eggs is examined under a dissecting microscope to confirm viability. Any eggs that are shrunken or with other indications of being nonviable are excluded.

Use five replicates of each test formulation and five control replicates. Prepare 5 cohorts of eggs for each treatment to be tested including the control treatments. Each cohort consists of 30 eggs (one to three hair shaft(s)) attached with duct tape to a wood applicator stick. Heat the test samples to 32 degrees Celsius in the waterbath. Insert the taped ends (hairs) of the applicator sticks into the test samples for 10 min of immersion. Wash the eggs in 900 mL of 32° C. tap water for 1 min by vigorous up and down movement of the applicator sticks with the hairs attached. Rinse the eggs with water from the wash bottle for min. Blot excess water with paper toweling. Transfer the hair with attached eggs to labeled petri dishes and incubate. Follow the same procedure for the control replications, except substitute tap water for the test solution.

When all control eggs have hatched (after approximately 12 days), examine all replicates under a dissecting microscope to determine the numbers hatching and failing to hatch. Failure to hatch is recorded as mortality. Categorize eggs failing to hatch as follows: (1) Early stage (no visible differentiation of the embryo when viewed under 30×); (2) Late stage (visible differentiation of embryo when viewed under 30×, typically eye spot is visible); and (3) Emergent (nymphal louse has opened operculum and begun to emerge, but died before emerging completely-part of nymph's body still within egg shell).

Calculate the percentage of control eggs failing to hatch; if this exceeds 15% the results should be discarded and the test repeated. Correct all counts of treated eggs failing to hatch by Abbott's Formula (corrected % killed=(% alive control−% alive treated)×100%+% alive control). Confirm that the corrected mortality experienced by the positive controls is 65 to 95%; if it is not, the results should be discarded and the test repeated.

TT-4301 versus water. A nit is considered "controlled" by a treatment when under any three of the categorizations, above (i.e., either the nit completely fails to emerge or the nit partially emerges, yet fails to obtain viability). 87.7% of nits treated with TT-4301 were controlled compared to only 10.9% of nits treated with water. Further, there was a 86.2% reduction of emerged nits in the treated group compared to the control group. Results from both in-vitro and in-vivo testing show TyraTech's head lice formula has significant activity against nits.

The foregoing specific but non-limiting examples are included herein to illustrate the present invention, but are prophetic, notwithstanding the numerical values, results and/or data referred to and contained therein.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein.

It is intended that the Specification and Example be considered as exemplary only, and not intended to limit the scope and spirit of the invention.

Unless otherwise indicated, all numbers expressing quantities of ingredients, properties such as reaction conditions, and so forth used in the application are to be understood as being modified in all instances by the term "about." Accordingly, unless indicated to the contrary, the numerical parameters set forth in the Application are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

Throughout this application, various publications are referenced. All such references are incorporated herein by reference.

What is claimed is:

1. A composition for controlling lice, the composition comprising:
   0.16 wt. % to 1.23 wt. % geraniol;
   0.30 wt. % to 2.25 wt. % isopropyl alcohol; and
   1.05 wt. % to 2.25 wt. % benzyl alcohol, wherein the wt. % is based on the total weight of the composition.

2. The composition for controlling lice of claim 1, further comprising linalool.

3. The composition for controlling lice of claim 2, comprising 0.16% to 0.96% linalool.

4. The composition for controlling lice of claim 1, further comprising glycerin.

5. A method for controlling lice comprising: applying an effective amount of the composition of claim 1 to a desired host, area, or object, wherein at least 1% of lice exposed to the composition die.

* * * * *